(12) United States Patent
Lu et al.

(10) Patent No.: US 9,688,747 B2
(45) Date of Patent: Jun. 27, 2017

(54) METHODS AND COMPOSITIONS FOR THE GENERATION AND USE OF CONFORMATION-SPECIFIC ANTIBODIES

(71) Applicant: Beth Israel Deaconess Medical Center, Inc., Boston, MA (US)

(72) Inventors: Kun Ping Lu, Newton, MA (US); Xiao Zhen Zhou, Newton, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 14/776,924

(22) PCT Filed: Mar. 14, 2014

(86) PCT No.: PCT/US2014/027017
§ 371 (c)(1),
(2) Date: Sep. 15, 2015

(87) PCT Pub. No.: WO2014/152157
PCT Pub. Date: Sep. 25, 2014

(65) Prior Publication Data
US 2016/0031977 A1   Feb. 4, 2016

Related U.S. Application Data

(60) Provisional application No. 61/792,588, filed on Mar. 15, 2013.

(51) Int. Cl.
*C07K 16/18* (2006.01)
*G01N 33/53* (2006.01)
*A61K 39/395* (2006.01)

(52) U.S. Cl.
CPC .......... *C07K 16/18* (2013.01); *C07K 2317/20* (2013.01); *C07K 2317/34* (2013.01); *C07K 2317/56* (2013.01); *C07K 2317/565* (2013.01); *C07K 2317/622* (2013.01); *C07K 2317/76* (2013.01)

(58) Field of Classification Search
CPC  C07K 16/18; C07K 2317/34; C07K 2317/56; C07K 2317/565; C07K 2317/622; C07K 2317/76; G01N 33/577; G01N 33/6896; G01N 2333/47; G01N 2800/28; G01N 2800/2821
See application file for complete search history.

(56) References Cited

U.S. PATENT DOCUMENTS

| | | | |
|---|---|---|---|
| 6,462,173 B1 | 10/2002 | Lu et al. | |
| 7,161,060 B1 | 1/2007 | Duff et al. | |
| 2002/0168684 A1 | 11/2002 | Comb et al. | |
| 2006/0258564 A1 | 11/2006 | Pluschke et al. | |
| 2008/0118505 A1 | 5/2008 | Tedder | |
| 2008/0248043 A1 | 10/2008 | Babcook et al. | |
| 2010/0260783 A1* | 10/2010 | Matsubara | C07K 16/18 424/172.1 |
| 2010/0278832 A1 | 11/2010 | Kamogawa et al. | |
| 2011/0104756 A1 | 5/2011 | Rodriguez et al. | |
| 2012/0183560 A1 | 7/2012 | Akassoglou | |
| 2013/0028900 A1 | 1/2013 | Lu et al. | |

FOREIGN PATENT DOCUMENTS

WO   WO-2012/149334 A2   11/2012

OTHER PUBLICATIONS

Padlan et al. Proc Natl. Acad. Sci. USA, 1989, 86:5938-5942.*
Paul WE, editor, Fundamental Immunology, Third Edition. Raven Press, New York, 1993, pp. 292-295.*
Rudikoff et al. Proc. Natl. Acad. Sci. USA, 1982, 79(6):1979-1983.*
International Preliminary Report on Patentability for International Application No. PCT/US2014/027017, issued Sep. 15, 2015 (13 pages).
International Search Report and Written Opinion for International Application No. PCT/US14/27017, mailed Oct. 28, 2014 (43 pages).
An et al., "Retention of the cis proline conformation in tripeptide fragments of bovine pancreatic ribonuclease a containing a non-natural proline analogue, 5,5-dimethylproline," J Am Chem Soc. 121(49):11558-66 (1999).
Nakamura, et al. "Proline isomer-specific antibodies reveal the early pathogenic tau conformation in Alzheimer's disease" Cell. 149(1):232-44 (2012).
Extended European Search Report for European Application No. 14768309.8, mailed Oct. 27, 2016 (11 pages).
Kondo et al., "cis p-tau: early driver of brain injury and tauopathy blocked by antibody," available in PMC Jan. 23, 2016, published in final edited form as: Nature. 523(7561):431-6 (2015) (37 pages).
Wolfe, "The role of tau in neurodegenerative diseases and its potential as a therapeutic target," Scientifica 2012:1-20 (2012).

* cited by examiner

*Primary Examiner* — Kimberly A. Ballard
(74) *Attorney, Agent, or Firm* — Clark & Elbing LLP; Kristina Bieker-Brady

(57) ABSTRACT

The present invention features methods and compositions for the generation and use of conformation-specific antibodies or fragments thereof.

14 Claims, 17 Drawing Sheets

US 9,688,747 B2

METHODS AND COMPOSITIONS FOR THE GENERATION AND USE OF CONFORMATION-SPECIFIC ANTIBODIES

CROSS-REFERENCE TO RELATED APPLICATIONS

This application claims the benefit of the filing date of U.S. Provisional Application No. 61/792,588, which was filed on Mar. 15, 2013, the contents of which are hereby incorporated by reference in its entirety.

STATEMENT AS TO FEDERALLY SPONSORED RESEARCH

This invention was made with government support under grants R01AG039405, R01CA167677, and R01CA122434, awarded by NIH. The government has certain rights in the invention.

BACKGROUND OF THE INVENTION

In general, the invention relates to methods and compositions for the generation and use of conformation-specific antibodies or fragments thereof.

Protein phosphorylation is a key cellular signaling mechanism that induces changes in protein conformation. For example, the phosphorylation of specific serine or threonine residues that immediately precede a proline residue (Ser/Thr-Pro motif) is a central regulatory mechanism in the cell. The unique stereochemistry of the proline residue means that the peptidyl-prolyl bond of the Ser/Thr-Pro motif can adopt two different conformational states (i.e., a cis conformation or a trans conformation). Peptidyl-prolyl cis/trans isomerases (PPIases) specifically catalyze the cis/trans isomerization of Ser/Thr-Pro motifs and, thus, regulate the structure of these proteins between the two distinct conformations.

Pin1 is a PPIase that specifically catalyzes the cis/trans isomerization of certain phosphorylated Ser/Thr-Pro (pSer/Thr-Pro) motifs. The identification of Pin1 as a phosphorylation-specific PPIase led to the understanding of a new signaling mechanism, whereby Pin1 catalytically regulates the conformation of its substrates after their phosphorylation to further control protein function. Moreover, Pin1 is tightly regulated by multiple mechanisms, and the deregulation of Pin1 plays a pivotal role in some human diseases.

The prevalence of Alzheimer's disease (AD) may quadruple worldwide by 2050, but currently there is no effective treatment. The AD hallmark lesions in the brain are senile plaques made of Aβ peptides and neurofibrillary tangles of phosphorylated tau (p-tau). Tau-related pathology (tauopathy) correlates well with progressive loss of neurons and memory in AD and is also a defining feature of many other tauopathies without Aβ pathology. While active and passive immunization against Aβ peptides have reached clinical trials, immunotherapy against p-tau has fallen far behind. Recent findings that active or passive immunization against tangle-containing p-tau epitopes reduces tau aggregates and improves memory deficits in mouse models and that tauopathy can spread the disease from neuron to neuron suggest that p-tau immunotherapy is a promising new approach to treating AD. However, since neuronal dysfunction occurs long before tangle formation, a major challenge is the development of immunotherapy targeting only the early pathogenic events that lead to tauopathy and memory loss in AD.

A very early event in tauopathy of AD is tau hyperphosphorylation notably on Ser/Thr-Pro motifs, which causes microtubule disruption and neurotoxicity. It has been found that phosphorylated Thr231-Pro motif in tau (pT231-tau) exists in the two distinct cis and trans conformations, and the prolyl isomerase Pin1 accelerates their conversion to inhibit tauopathy. Pin1-null mice displayed age-dependent tauopathy, whereas Pin1 overexpression inhibits tauopathy in a mouse model of AD. In human MCI and AD neurons, Pin1 is inhibited by multiple mechanisms, whereas the Pin1 SNP that prevents its down-regulation is associated with delayed AD onset. It has also been found that human Pin1 located at 19p13.2 is associated with late-onset AD, that pT231-tau is at the beginning of sequential p-tau epitopes in pretangle neurons, and that CSF pT231-tau is an early biomarker that correlates with memory loss and tracks MCI conversion to AD, and distinguishes AD from frontotemporal dementia (FTD). Thus, pT231-tau is a very early disease-initiating event in AD.

Veteran soldiers returning from war experience distinctive traumatic brain injury (TBI) features that are the same as neurodegenerative disease reported previously in athletes who have sustained multiple concussions. It appears that TBI in these people can trigger the development of chronic traumatic encephalopathy (CTE), a devastating neurodegenerative disorder, for which there is no known treatment. The neuropathological hallmark of CTE is the widespread abnormal accumulation of hyperphosphorylated tau (p-tau) as neurofibrillary tangles (tauopathy), similar to the hallmark lesion seen in Alzheimer's disease (AD) and other tauopathies. Thus, immunotherapy against p-tau is proving to be a new option for treating tauopathies. More specifically, there exists a need in the art for conformation-specific antibodies that specifically bind to a cis or trans conformation of p-tau to target the early pathogenic pretangle tau modifications leading to tauopathy.

SUMMARY OF THE INVENTION

The invention features an isolated conformation-specific binding moiety, optionally an antibody or a monoclonal antibody, wherein the binding moiety includes one or more heavy chain variable regions with SEQ ID NOs:1-3, or variants thereof and one or more light chain variable regions with SEQ ID NOs:4-6, or variants thereof. In one embodiment, the isolated binding moiety includes two or more heavy chain variable regions with SEQ ID NOs:1-3, or variants thereof and two or more light chain variable regions with SEQ ID NOs:4-6, or variants thereof. In a second embodiment, the isolated binding moiety includes heavy chain variable regions with SEQ ID NOs:1-3, or variants thereof and light chain variable regions with SEQ ID NOs:4-6, or variants thereof. In a third embodiment, the isolated monoclonal antibody includes a heavy chain protein sequence of SEQ ID NO:22 and a light chain protein sequence of SEQ ID NO:23.

The invention also features an isolated conformation-specific binding moiety, optionally an antibody or a monoclonal antibody, wherein the binding moiety includes one or more heavy chain variable regions with SEQ ID NOs:7-9, or variants thereof and one or more light chain variable regions with SEQ ID NOs:10-12, or variants thereof. In one embodiment, the isolated binding moiety includes two or more heavy chain variable regions with SEQ ID NOs:7-9, or variants thereof and two or more light chain variable regions with SEQ ID NOs:10-12, or variants thereof. In a second embodiment, the isolated binding moiety includes heavy chain variable regions with SEQ ID NOs:7-9, or variants thereof and light chain variable regions with SEQ ID NOs: 10-12, or variants thereof. In a third embodiment, the isolated monoclonal antibody includes a heavy chain protein sequence of SEQ ID NO:24 and a light chain protein sequence of SEQ ID NO:25

In one aspect of the invention, the isolated binding moiety described above bind specifically to the cis conformation of phosphorylated-Threonine231-tau protein (pT231-tau). In another aspect of the invention, the isolated monoclonal antibodies described above are single chain antibodies or antibody fragments thereof. In yet another aspect, the isolated monoclonal antibodies are chimeric antibodies, a humanized antibodies, or human antibodies. In all aspects of the invention, the isolated binding moieties are formulated into pharmaceutical composition including a pharmaceutically acceptable carrier.

In another aspect, the invention also features a method of treating a tauopathy, traumatic brain injury (TBI), or stroke, the method including administering to a subject in need thereof the binding moieties described above, in an amount sufficient to treat the tauopathy, TBI, or stroke, wherein the monoclonal antibody specifically binds to the cis conformation of pT231-tau.

The invention further features a method for monitoring a therapeutic response in a subject treated with the binding moieties described herein the method including: a.) determining the level of cis pT231-tau or cis:trans pT231-tau ratio in a sample obtained from the subject, and optionally b.) determining the levels of CSF t-tau, pT181-tau, Aβ42, or ApoE4, wherein a decrease in the level of cis pT231-tau or cis:trans pT231-tau ratio results in an effective therapeutic response to the binding moieties, and/or wherein the levels of CSF t-tau, pT181-tau, Aβ42, or ApoE4 is decreased.

The invention also features a method of diagnosing a subject as having or having a predisposition to a tauopathy, the method including: a.) determining the level of cis pT231-tau or cis:trans pT231-tau ratio in a sample obtained from the subject, b.) comparing the level of cis pT231-tau or cis:trans pT231-tau ratio in the sample with a normal reference sample, wherein an elevated level of cis pT231-tau or an increase in cis:trans pT231-tau ratio as compared to the normal reference sample results in diagnosing the subject as having, or having a predisposition to the tauopathy, and administering to the subject the binding moieties of the invention, wherein the binding moieties specifically bind the cis pT231-tau in an amount sufficient to treat the tauopathy.

In all aspects of the invention, the tauopathy is selected from the group consisting of: progressive supranuclear palsy, chronic traumatic encephalopathy (CTE), frontotemporal dementia, frontotemporal lobar degeneration, Lytico-Bodig disease, tangle-predominant dementia, meningioangiomatosis, subacute sclerosing panencephalitis, Pick's disease, corticobasal degeneration, and Alzheimer's disease. In certain aspects, the subject is predisposed to or is at an early stage of the tauopathy, wherein the predisposition or early stage of the tauopathy is determined by an elevated level of cis pT231-tau or an increase in cis:trans pT231-tau ratio in a sample obtained from the subject. In other aspects, the predisposition or early stage of the tauopathy is also determined by the levels of CSF t-tau, pT181-tau, Aβ42, or ApoE4 levels. In yet another aspect, the subject is predisposed by a history of repeated brain trauma. In all aspects of the invention the sample is selected from the group consisting of: urine, blood, serum, plasma, saliva, amniotic fluid, and cerebrospinal fluid (CSF).

The invention further features an isolated conformation-specific binding moiety, optionally an antibody or a monoclonal antibody, wherein the binding moiety includes one or more heavy chain variable regions with SEQ ID NOs:13-15, or variants thereof and one or more light chain variable with SEQ ID NOs:16-18, or variants thereof. In one embodiment, the isolated binding moiety includes two or more heavy chain variable regions with SEQ ID NOs:13-15, or variants thereof and two or more light chain variable with SEQ ID NOs:16-18, or variants thereof. In a second embodiment, the isolated binding moiety includes heavy chain variable regions with SEQ ID NOs:13-15, or variants thereof and light chain variable with SEQ ID NOs:16-18, or variants thereof. In a third embodiment, the isolated monoclonal antibody includes a heavy chain protein sequence of SEQ ID NO:26 and a light chain protein sequence of SEQ ID NO:27.

The invention also features an isolated conformation-specific binding moiety, optionally an antibody or a monoclonal antibody, wherein the binding moiety includes one or more light chain variable regions with SEQ ID NOs:19-21, or variants thereof. In one embodiment, the isolated binding moiety include two or more light chain variable regions with SEQ ID NOs:19-21, or variants thereof. In a second embodiment, the isolated binding moiety includes light chain variable regions with SEQ ID NOs:19-21, or variants thereof. In a third embodiment, the isolated monoclonal antibody includes a light chain protein sequence of SEQ ID NO:28.

In a certain aspect of the invention, the isolated binding moieties described above bind specifically to the trans conformation of pT231-tau. In another aspect, the isolated monoclonal antibodies are single chain antibodies or antibody fragments thereof. In yet another aspect, the isolated monoclonal antibodies are chimeric antibodies, humanized antibodies, or human antibodies. In another aspect, the binding moieties described above are formulated as pharmaceutical compositions including a pharmaceutically acceptable carrier.

Finally, the invention also features a kit for diagnosing a subject as having or having a predisposition to a tauopathy including: the binding moieties described herein that bind specifically to the cis conformation of pT231-tau, the binding moieties described herein that bind specifically to the trans conformation of pT231-tau and instructions for the use of the binding moieties for diagnosing the subject as having or having a predisposition to the tauopathy.

By "adjuvant" is meant one or more substances that cause stimulation of the immune system. In this context, an adjuvant is used to enhance an immune response to one or more vaccine antigens or antibodies. An adjuvant may be administered to a subject before, in combination with, or after administration of the vaccine. Examples of chemical compounds used as adjuvants include, but are not limited to, aluminum compounds, oils, block polymers, immune stimulating complexes, vitamins and minerals (e.g., vitamin E, vitamin A, selenium, and vitamin B12), Quil A (saponins), bacterial and fungal cell wall components (e.g., lipopolysaccharides, lipoproteins, and glycoproteins), hormones, cytokines, and co-stimulatory factors.

By "amount sufficient" is meant an amount that, when administered to a subject suffering from a disorder (e.g., a tauopathy, tramatic brain injury (TBI), stroke, or other neurological disorder), is sufficient to cause a qualitative or quantitative reduction in the symptoms associated with the disorder.

By "antibody" is meant monoclonal antibodies, polyclonal antibodies, humanized antibodies, chimeric antibodies, recombinant antibodies, multispecific antibodies, and antibody fragments. The antibody may be, for example, a conformation-specific antibody (e.g., an antibody that binds to the cis or trans conformation of a Xaa-Pro motif, wherein Xaa is an amino acid). An antibody specifically binds to an antigen. The antibody may also be a non-immunoglobulin binding polypeptide.

By "antigen" is meant a molecule to which an antibody can selectively bind. The target antigen may be a protein (e.g., an antigenic peptide), carbohydrate, nucleic acid, lipid, hapten, or other naturally occurring or synthetic compound. The target antigen may be a polypeptide (e.g., a polypeptide containing a Xaa-Pro motif (e.g., a phosphorylated or non-phosphorylated Ser/Thr-Pro motif)) or peptide mimics (e.g., a polypeptide containing a Xaa-homoproline motif (e.g., a phosphorylated or nonphosphorylated Ser/Thr-homoproline motif)). An antigen may also be administered to an animal to generate an immune response in the animal.

By "binding affinity" is meant the strength of the total noncovalent interactions between a single binding site of a molecule (e.g., an antibody) and its binding partner (e.g., an antigen or antigenic peptide). Unless otherwise indicated, as used herein, "binding affinity" refers to intrinsic binding affinity, which reflects a specific interaction between members of a binding pair (e.g., antibody and antigen). The affinity of a molecule X for its partner Y can generally be represented by the dissociation constant ($K_d$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

By "binding moiety" is meant an antibody (e.g., a polyclonal antibody, a monoclonal antibody, a humanized antibody, a chimeric antibody), a human antibody, antibody fragment, receptor, ligand, a non-immunoglobulin binding polypeptide, or small molecule portion of an agent that specifically binds to a target molecule (e.g., a polypeptide, protein (e.g., cis pT231-tau or trans pT231-tau), or conjugate including same) or to a cell or tissue bearing the target molecule (e.g., a cell surface antigen, e.g., a receptor or ligand).

By "biological sample" or "sample" is meant solid and fluid samples. Biological samples may include cells, protein or membrane extracts of cells, blood or biological fluids including, e.g., ascites fluid or brain fluid (e.g., cerebrospinal fluid (CSF)). Examples of solid biological samples include samples taken from feces, the rectum, central nervous system, bone, breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, and the thymus. Examples of biological fluid samples include samples taken from the blood, serum, CSF, semen, prostate fluid, seminal fluid, urine, saliva, sputum, mucus, bone marrow, lymph, and tears. Samples may be obtained by standard methods including, e.g., venous puncture and surgical biopsy. In certain embodiments, the biological sample is a breast, lung, colon, or prostate tissue sample obtained by needle biopsy.

By "conformation-specific antibody" is an antibody or fragment thereof that recognizes and specifically binds to a particular conformation (e.g., a conformational isomer or conformer) of its complementary antigen. For example, as described herein, the conformation-specific antibody may specifically bind to the cis conformation of a Xaa-Pro motif (e.g., cis pT231-tau), but will not specifically bind to the trans conformation of the Xaa-Pro motif (e.g., trans pT231-tau), where Xaa is any amino acid residue (e.g., serine or threonine). In this case, the conformation-specific antibody will have, for example, at least 10- to 100-fold greater affinity to the cis conformation than to the trans conformation of a Xaa-Pro motif. Conversely, the conformation-specific antibody may specifically bind to the trans conformation of a Xaa-Pro motif, but will not specifically bind to the cis conformation of the Xaa-Pro motif, where Xaa is any amino acid residue (e.g., serine or threonine). In certain embodiments, the Ser/Thr-Pro motif may be phosphorylated (i.e., pSer/Thr-Pro).

By "disorder" is meant any condition that may be treated, inhibited, diagnosed, or screened for according to the methods of the invention described herein.

By "fragment" is meant a portion of a nucleic acid or polypeptide (e.g., an antibody) that contains at least, e.g., 10%, 20%, 30%, 40%, 50%, 60%, 70%, 80%, 90%, 95%, or more of the entire length of the nucleic acid or polypeptide. A nucleic acid fragment may contain, e.g., 10, 20, 30, 40, 50, 60, 70, 80, 90, or 100, 200, 300, 400, 500, 600, 700, 800, 900, 1000, 1100, 1200, 1300, 1400, 1500, 2000, 2500, 3000, 4000, 4500, or 5000 nucleotides or more nucleotides, up to the full length of the nucleic acid. A polypeptide fragment may contain, e.g., 10, 20, 30, 40, 50, 60, 70, 80, 90, 100, 150, 200, 250, 300, 350, 400, 450, or 500 amino acids or more amino acids, up to the full length of the polypeptide. Fragments useful in the therapeutic methods of the invention include, e.g., fragments of conformation-specific antibodies that retain biological activity (e.g., fragments that bind to a specific conformational state). Fragments can be modified as described herein and as known in the art.

By "humanized antibody" is meant an immunoglobulin amino acid sequence variant or fragment thereof that is capable of binding to a predetermined antigen. The antibody may contain both the light chain, as well as at least the variable domain of a heavy chain. The antibody also may include the CH1, hinge, CH2, CH3, or CH4 regions of the heavy chain. The humanized antibody comprises a framework region (FR) having substantially the amino acid sequence of a human immunoglobulin and a complementarity determining region (CDR) having substantially the amino acid sequence of a non-human immunoglobulin.

Generally, a humanized antibody has one or more amino acid residues introduced into it from a source that is non-human. In general, the humanized antibody may comprise substantially all of at least one, and typically two, variable domains (e.g., Fab, Fab', F(ab')$_2$, Fabc, or Fv) in which all or substantially all of the CDR regions correspond to those of a non-human immunoglobulin and all or substantially all of the FR regions are those of a human immunoglobulin consensus sequence. The humanized antibody may comprise at least a portion of an immunoglobulin constant region (Fc), typically that of a human immunoglobulin. By "complementarity determining region (CDR)" is meant the three hypervariable sequences in the variable regions within each of the immunoglobulin light and heavy chains. By "framework region" is meant the sequences of amino acids located on either side of the three hypervariable sequences of the immunoglobulin light and heavy chains. See, e.g., Jones et al., Nature 321:522-525 (1986); Riechmann et al., Nature 332:323-329 (1988); and Presta, Curr. Op. Struct. Biol. 2:593-596 (1992), and U.S. Pat. Nos. 4,816,567 and 5,530,101, hereby incorporated by reference.

The term "monoclonal antibody," as used herein, refers to an antibody obtained from a population of substantially homogeneous antibodies (i.e., the individual antibodies comprising the population are identical except for possible naturally occurring mutations that may be present in minor amounts). Monoclonal antibodies are highly specific, being directed against a single antigenic site. Furthermore, in contrast to conventional (e.g., polyclonal) antibody preparations, which typically include different antibodies directed against different determinants (e.g., epitopes), each monoclonal antibody is directed against a single determinant on the antigen. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by the hybridoma method first described by Kohler et al. (see, e.g., *Nature* 256: 495, 1975) or may be made by recombinant DNA methods (see, e.g., U.S. Pat. No. 4,816,567). Monoclonal antibodies may also be isolated from phage antibody libraries using the techniques described in Clackson et al. (*Nature* 352: 624-628, 1991) and Marks et al. (*J. Mol. Biol.* 222: 581-597, 1991), for example.

By "neurological disorder" is meant a disturbance in the structure or function of the nervous system resulting from a developmental abnormality, disorder, injury, or toxin. Exemplary neurological disorders include Alzheimer's disease (AD), mild cognitive impairment (MCI), Parkinson's disease (PD), multiple sclerosis (MS), muscular dystrophy, corticobasal degeneration, dementia pugilistica, Down's syndrome, frontotemporal dementias, myotonic dystrophy, Niemann-Pick disease, Pick's disease, prion disease, progressive supranuclear palsy, subacute sclerosing panencephalistis, convulsive disorders (e.g., epilepsy), vascular dementia, age-related dementia, head trauma, stroke, neurofibromatosis, Lewy body disease, amyotrophic lateral sclerosis (ALS), peripheral neuropathies, and macular degeneration.

By "pharmaceutically acceptable carrier" is meant a carrier that is physiologically acceptable to the treated subject while retaining the therapeutic properties of the composition (e.g., the conformation-specific antibody) with which it is administered. One exemplary pharmaceutically acceptable carrier substance is physiological saline. Other physiologically acceptable carriers and their formulations are known to one skilled in the art and are described, for example, in Remington's Pharmaceutical Sciences (20$^{th}$ edition, ed. A. Gennaro, 2000, Lippincott, Williams & Wilkins, Philadelphia, Pa.).

By "protein," "polypeptide," "polypeptide fragment," or "peptide" is meant any chain of more than two amino acid residues, regardless of post-translational modification (e.g., glycosylation or phosphorylation), constituting all or part of a naturally occurring polypeptide or peptide or constituting a non-naturally occurring polypeptide or peptide. A polypeptide or peptide may be said to be "isolated" or "substantially pure" when physical, mechanical, or chemical methods have been employed to remove the polypeptide from cellular constituents. An "isolated polypeptide" (e.g., an isolated antibody), "substantially pure polypeptide," or "substantially pure and isolated polypeptide" is typically considered removed from cellular constituents and substantially pure when it is at least 60% by weight free from the proteins and naturally occurring organic molecules with which it is naturally associated. The polypeptide may be at least 75%, 80%, 85%, 90%, 95%, or 99% by weight pure. A substantially pure polypeptide (e.g., a substantially pure antibody or fragment thereof) may be obtained by standard techniques, for example, by extraction from a natural source (e.g., cell lines or biological fluids), by expression of a recombinant nucleic acid encoding the polypeptide, or by chemically synthesizing the polypeptide. Purity can be measured by any appropriate method, e.g., by column chromatography, polyacrylamide gel electrophoresis, or HPLC analysis. Alternatively, a polypeptide is considered isolated if it has been altered by human intervention, placed in a location that is not its natural site, or if it is introduced into one or more cells.

The peptides and polypeptides of the invention, as defined above, include all "mimetic" and "peptidomimetic" forms. The terms "mimetic" and "peptidomimetic" refer to a synthetic chemical compound that has substantially the same structural and/or functional characteristics of the peptides (e.g., antigenic peptides) or polypeptides of the invention. The mimetic can be either entirely composed of synthetic, non-natural analogs of amino acids or may be a chimeric molecule of natural amino acids and non-natural analogs of amino acids. The mimetic can also incorporate any amount of conservative substitutions, as long as such substitutions do not substantially alter the mimetic's structure or activity.

By "decrease" is meant the ability to cause an overall reduction of 20% or greater, of 50% or greater, or of 75%, 80%, 85%, 90%, 95%, or greater. For therapeutic applications, to "decrease" can refer to the reduction in the level of polypeptides or proteins associated with the disorder (e.g., a tauopathy, TBI, or stroke). For diagnostic or monitoring applications, to "decrease" can refer to a decrease in the level of protein or nucleic acid detected by the diagnostic or monitoring assays.

By "elevated or increase" is meant an increase in gene expression or protein expression, as compared to a control from a normal or reference sample (e.g., an increase of at least 2-fold, e.g., from about 2-fold to about 150-fold, e.g., from 5-fold to 150-fold, from 5-fold to 100-fold, from 10-fold to 150-fold, from 10-fold to 100-fold, from 50-fold to 150-fold, from 50-fold to 100-fold, from 75-fold to 150-fold, or from 75-fold to 100-fold, as compared to a control or a normal reference sample). An increase or decrease in gene expression or protein expression can be determined using any useful methods known in the art or described herein (e.g., as determined by PCR, gel electrophoresis, ELISA).

By "reference" is meant any sample, standard, or level that is used for comparison purposes. A "normal reference sample" can be a prior sample taken from the same subject prior to the onset of a disorder (e.g., a tauopathy, traumatic brain injury (TBI), stroke, or other neurological disorder), a sample from a subject not having the disorder, a subject that has been successfully treated for the disorder, or a sample of a purified reference polypeptide at a known normal concentration. By "reference standard or level" is meant a value or number derived from a reference sample. A normal reference standard or level can be a value or number derived from a normal subject that is matched to a sample of a subject by at least one of the following criteria: age, weight, disease stage, and overall health. In one example, a normal reference level of, for example, a polypeptide indicative of a disorder or a conformation of a polypeptide indicative of a disorder, is less than 5 ng/ml in a serum sample, less than 4 ng/ml, less than 3 ng/ml, less than 2 ng/ml, or less than 1 ng/ml in a serum sample. A "positive reference" sample, standard, or value is a sample, standard, value, or number derived from a subject that is known to have a disorder (e.g., a tauopathy, TBI, stroke, or other neurological disorder) that is matched to a sample of a subject by at least one of the following criteria: age, weight, disease stage, and overall health. For example, a positive reference value for, e.g., a polypeptide indicative of a disorder, is greater than 5 ng/ml serum, greater than 10 ng/ml serum, greater than 20 ng/ml, greater than 30 ng/ml, greater than 40 ng/ml, or greater than 50 ng/ml serum.

By "specifically binds" is meant a molecule (e.g., an antibody) which recognizes and binds another molecule (e.g., an antigen), but that does not substantially recognize and bind other molecules. In one example, an antibody that specifically binds the cis conformation of pT231-tau does not specifically bind the trans conformation of pT231-tau. The term "specific binding," "specifically binds to," or is "specific for" a particular molecule (e.g., a polypeptide, an epitope on of a polypeptide, or a conformation of a polypeptide), as used herein, can be exhibited, for example, by a molecule having a $K_d$ for the molecule to which it binds of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or greater.

The term "specifically binds" may also refer to binding where a molecule (e.g., an antibody) binds to a particular polypeptide (e.g., a polypeptide containing a Xaa-Pro motif, where Xaa is any amino acid residue (e.g., serine or threonine)), an epitope on a particular polypeptide, or a conformation of a particular polypeptide (e.g., a cis conformation of a Xaa-Pro motif, e.g., cis pT231-tau) without substantially binding to any other polypeptide, polypeptide epitope, or polypeptide conformation (e.g., the trans conformation of a Xaa-Pro motif, e.g., trans pT231-tau). For example, the conformation-specific antibody may have, for example, at least 10- to 100-fold greater affinity (e.g., $10^1$-, $10^2$-, $10^3$-, $10^4$-, $10^5$-, $10^6$-, $10^7$-, $10^8$-, $10^9$-, or $10^{10}$-fold greater affinity) to one conformation (e.g., the cis conformation) than to another conformation (e.g., the trans conformation) of, for example, a Ser/Thr-Pro motif.

By "subject" is meant a mammal, including, but not limited to, a human or non-human mammal, such as a bovine, equine, canine, ovine, or feline.

By "treating" is meant administering a pharmaceutical composition for therapeutic purposes or administering treatment to a subject already suffering from a disorder to improve the subject's condition. By "treating a tauopathy, TBI, or stroke" is meant that the symptoms associated with the tauopathy, TBI, or stroke are, e.g., alleviated, reduced, cured, or placed in a state of remission.

By "variant CDRs" is meant the CDRs can be varied at single amino acid positions (e.g., 1, 2, 3, 4, 5, or more amino acid substitutions) or combined with different CDRs from heavy chain and light chain (e.g., combinations of CDR1 and 3 in the heavy chain with CDR1 and 2 in the light chain). Such variants can have substitutions (either exemplary or preferred) as described herein. Variant CDRs would preferably retain residues conserved between the depicted antibodies described herein while have changes in residues shown to vary between antibodies. Binding moieties containing variant CDRs will retain their ability to specifically bind a cis (or trans) conformation of the p-Tau epitope as described herein.

Other features and advantages of the invention will be apparent from the following detailed description, the drawings, and the claims.

BRIEF DESCRIPTION OF THE DRAWINGS

FIG. 3D shows the ability of cis and trans mAbs to recognize pT231-tau on immunoblots confirmed using small molecules that induced Pin1 degradation (Cpd1 is more potent than Cpd1E, with the inactive Cpd1A analog used as control). FIG. 3E shows the immunoglobulin isotypes of mAbs as determined using an isotyping ELISA kit.

In FIGS. 5A and 5B, SY5Y cells were transfected with tau and p25/Ckd5, followed by addition of mAbs to the medium before subjecting to staining with anti-mouse antibodies (light smears surrounding the circles). Cis mAbs were shown to reach neuritis (FIG. 5A) and trans mAbs were shown to reach the cell body (FIG. 5B). FIG. 5C is a blot showing that cis mAb reduced tau levels of endogenous and exogenous tau, but not T231A, only when p25/Cdk5 was co-transfected in SY5Y cells. FIG. 5D is a blot showing that cis mAbs reduced tau in Tau-Tg mouse brain slices ex vivo. FIG. 5E is a blot showing serum depleted SY5Y cells with or without cis or trans mAb. Cis mAb potently reduced cis pT231-tau, while trans mAb reduced transpT231-tau. IgG heavy and light chains showed that cis and trans mAb entered cells and actin as loading control.

FIG. 6A shows SY5Y cells transfected with p25, Cdk5, and tau+GFP and FIGS. 6B and 6C show SY5Y cells transfected with GFP-tau or T231A tau mutant followed by addition of cis or trans pT231-tau mAb before subjecting to immunostaining for microtubules (MT) and nuclei for microtuble disruption (FIG. 6A) and neurotoxicity (FIG. 6B). The results from immunostaining were confirmed by time-lapse live-cell confocal imaging in FIG. 6C. FIG. 6D are immunostaining images for MT of SY5Y cells subjected to serum depletion in the presence of cis or trans mAb for 72 hours. FIG. 6E are immunostaining images of cell morphology showing neurotoxicity of SY5Y cells subjected to serum depletion in the presence of cis or trans mAb for 72 hours.

FIG. 7A shows cis and trans pT231-tau in cerebrospinal fluid (CSF) from 8 healthy controls and five advanced AD patients assayed by ELISA using cis- and trans antibodies. FIG. 7B shows the cis/trans ratios (nd:not detectable, na:not applicable).

FIG. 15A is a blot showing that cis p-tau increases with TBI severity, as shown by immunoblotting of brain samples 2 weeks after TBI with different weight drop heights. FIGS. 15B and 15C are immunostaining results showing that robust cis, but not trans, p-tau appeared after TBI in a time-dependent manner, as shown by immunostaining for cis or trans p-tau and DNA. FIG. 15D shows the presence of robust cis p-tau, but not ATB, TG3, AT100, or PHF1 in brains 2 weeks after TBI.

DETAILED DESCRIPTION

Figure 1:
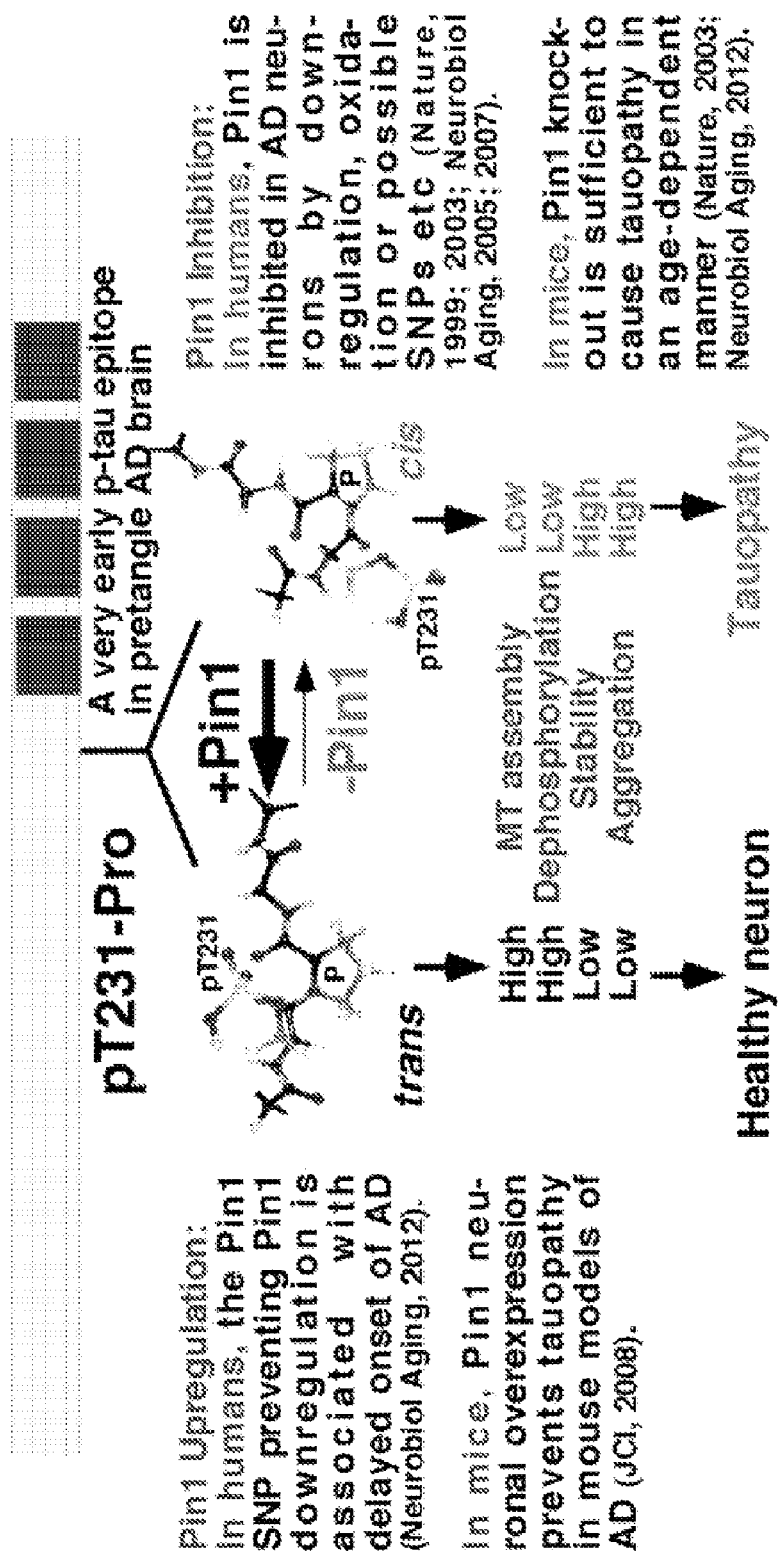
FIG. 1 is a chart showing that Pin1-catalyzed cis to trans isomerization of pT231-tau protects against tauopathy in Alzheimer's Disease (AD), as shown by manipulating Pin1 in vitro, in cell models, ex vivo and mouse models, and analyzing SNP association with AD.

In general, the invention relates to methods and compositions for the generation and use of conformation-specific antibodies or fragments thereof. We have discovered that cis but not trans pT231-tau is an extremely early pathogenic conformation leading to tauopathy and memory loss in AD. We have developed a quantitative ELISA assay to show that the cis p-tau was undetectable in control cerebrospinal fluid (CSF), that both cis and trans p-tau were elevated in AD, with cis levels much higher than trans, and the cis:trans ratios were increased and similar in AD patients. These results together with the generation of conformation-specific antibodies described herein provide a novel approach to diagnosing and treating AD and other tauopathies at an early pathogenic stage by detecting the cis pT231-tau with the trans pT231-tau as internal control.

PPIases and the Cis/Trans Conformation of PPIase Substrates

Proline is an amino acid residue unique in its ability to adopt either the cis or trans conformation. Due to the relatively large energy barrier of its isomerization ($\epsilon^u$=14 to 24 kcal mol$^{-1}$), uncatalyzed isomerization is a slow process, but may be accelerated by PPIases. PPIases facilitate protein folding and include, for example, cyclophilins (Cyps), FK506-binding proteins (FKBPs), and parvulin-like PPIases (e.g., Ess1 and Pin1).

Pin1 (protein interacting with NIMA (never in mitosis A)-1) specifically isomerizes phosphorylated Ser/Thr-Pro (pSer/Thr-Pro) motifs of certain polypeptides, which is important because proline-directed kinases (e.g., protein kinases that phosphorylate certain Ser/Thr residues that precede a proline residue) and phosphatases are conformation-specific and generally act only on the trans conformation. Pin1 has a two-domain structure that includes an N-terminal WW domain and a C-terminal PPIase domain, and structure-function analyses have shown that the unique substrate specificity of Pin1 towards specific pSer/Thr-Pro motifs results from interactions provided by both the WW domain and the PPIase domain. The PPIase activity of Pin1 facilitates the regulation of, for example, growth-signal responses, cell-cycle progression, cellular stress responses, neuronal function, and immune responses.

Exemplary substrates of Pin1, each containing motifs capable of being isomerized, are listed in Table 1. The functional consequences of isomerization of the substrates are also listed.

TABLE 1

Pin1 Substrates

| Substrate (GenBank Accession Number) | Targeting Site(s) | Functional Consequence of PPlase Activity of Pin1 Upon Substrate |
|---|---|---|
| \multicolumn{3}{c}{G2/M and Mitotic Regulation} | | |
| NIMA (P11837) | — | Regulation of mitotic function |
| RAB4 (NP_004569) | — | — |
| CDC25 (AAA58417) | pThr48/67-Pro | Dephosphorylation and regulation of activity |
| WEE1 (NP_003381) | pT186-P | Inhibition of WEE1 activity |
| PLK1 (P53350) | — | — |
| MYT1 (NP_004194) | — | — |
| CDC27 (AAH11656) | — | — |
| CENP-F (P49454) | — | — |
| Incenp (NP_064623) | — | — |
| RPB1 (CAA65619) | pSer5-Pro | Regulation of CTD dephosphorylation |
| NHERF-1 (AAA80218) | pSer279/301-P | Dephosphorylation |
| KRMP1 (NP_057279) | pT-1604-P | Regulation of mitotic function |
| CK2 (NP_808227) | Multiple pSer/Thr-Pro sites | Inhibition of kinase activity |
| TopoIIα (NP_001058) | — | Inhibition or induction of phosphorylation |
| DAB2 (NP_001334) | — | Dephosphorylation |
| p54nrb (CAA72157) | Multiple pSer/Thr-Pro sites | — |
| Sil (CAC14001) | Multiple pSer/Thr-Pro sites | Regulation of function |
| EMI1 (NP_036309) | pS10-P | Stabilization |
| \multicolumn{3}{c}{G1/S Regulation} | | |
| Cyclin D1 (NP_444284) | pT286-P | Stabilization and nuclear localization |
| Ki67 | pT234-P | — |
| c-Myc (CAA46984) | pT58-P | Dephosphorylation and destabilization |
| Cyclin E (P24864) | pS384-P | Destabilization |
| \multicolumn{3}{c}{Growth and Oncogenic Signaling} | | |
| c-Jun (AAH06175) | pS63/73-P | Transactivation |
| B-catenin (P35222) | pS246-P | Stabilization, protein interaction, and transactivation |
| Cf-2 (NP_034298) | — | Destabilization |
| NF-κB (AAH33210) | pT254-P | Stabilization, protein interaction, and transactivation |
| RAF1 (AAA60247) | Multiple pSer/Thr-Pro sites | Dephosphorylation and prolonging activation |
| c-Fos (CAA24756) | Multiple pSer/Thr-Pro sites | Transactivation |
| RARα (NP_001019980) | pS77-P | Stabilization and transactivation |
| AIB1/SRC-3 | — | Transactivation and destabilization |
| HBx (NP_110380) | pS41-P | Stabilization and potentiation |
| STAT3 (NP_998827) | pS727-P | Transactivation |
| \multicolumn{3}{c}{DNA Damage, Oxidative Stress Response, and Apoptosis} | | |
| p53 (BAC16799) | Multiple pSer/Thr-Pro sites | Stabilization and transactivation |
| Bcl-2 (NP_000648) | pS70/87-P | — |
| p73 (CAA72221) | Multiple pSer/Thr-Pro sites | Stabilization and transactivation |
| BimEL (AAC39593) | pS65-P | Stabilization |
| p66$^{Shc}$ (AAH14158) | — | Mitochondrial import |
| CHE1 (P06276) | — | Destabilization |
| \multicolumn{3}{c}{Neuronal Survival and Degeneration} | | |
| Tau (NP_058519) | pT231-P pT212-P | Dephosphorylation and protein interaction |
| APP (P05067) | pT668-P | Promotes non-amyloidogenic APP processing and reduces Aβ production |
| APP fragment | pT668-P | Increases Aβ production from C99 APP fragment |
| Synphilin-1 (AAD30362) | pS211/215-P | Protein interaction |
| Gephyrin (CAC81240) | pS188/194/200-P | Protein interaction |
| MCL1 (CAl15504) | pT163-P | Stabilization |
| \multicolumn{3}{c}{Immune Response and Asthma} | | |
| NFAT (NP_666017) | — | — |
| AUF1 (NP_112738) | — | Protein interaction |
| IRF3 (AAH71721) | pS339-P | Destabilization |
| BTK (CAl42359) | pS21/115-P | Destabilization |
| \multicolumn{3}{c}{Others} | | |
| SIN2-RPD3 | — | Reduces histone deacetylases |
| hSpt5 (NP_001124297) | — | — |

Figure 2:
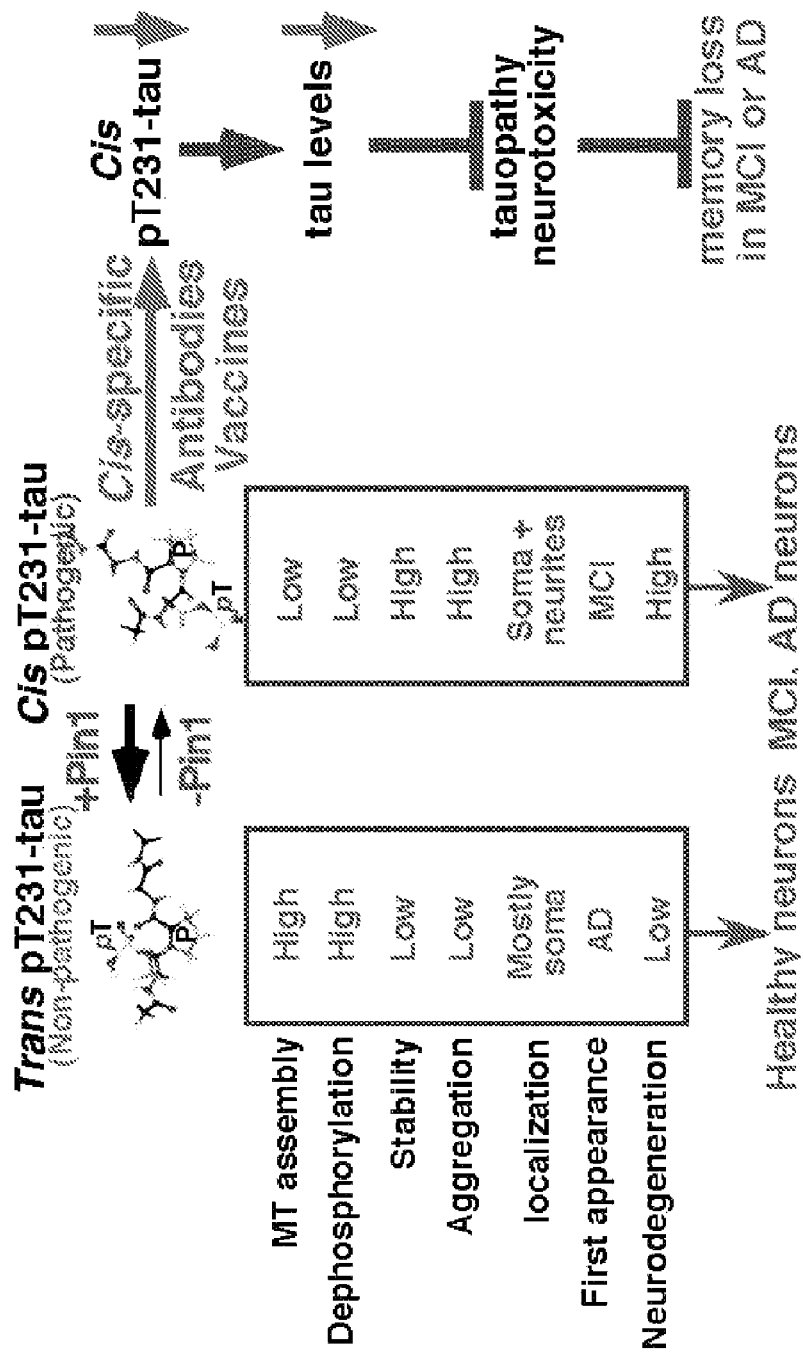
FIG. 2 is a chart showing that development of cis- and trans-specific antibodies reveals that cis, but not trans pT231-tau loses normal tau function and gains toxic function, and is the early pathogenic conformation leading to tauopathy and memory loss in mild cognitive impairment (MCI) and AD. Pin1 prevents the accumulation of cis pT231-tau by converting it to the non pathological trans.

The importance of phosphorylation-independent prolyl isomerization has also been documented. For example, the PPIase CypA catalyzes the cis-trans isomerization of the prolyl bond at position Gly237-Pro238 of the Crk protein. Other PPIase substrates isomerized in a phosphorylation-independent manner include, without limitation, steroid receptors, c-Myb, H3P30, H3P38, Itk, 5-hydroxytryptamine type 3 (5-HT3) receptors, the phage tip protein G3P, the Gag polyprotein of the human immunodeficiency virus-1 (HIV-1) virion, intracellular calcium release channel, CrkII/CrkL proteins, centrosome protein 55 kDa (Cep55), the retroviral Rel proteins, PKB/Akt, human T-cell leukemia virus type 1 (HTLV-1) Tax oncoprotein, Stat3, HER2/Neu, Notch, FAK, FOXO, PML, C/EBP, and SMRT. Deregulation of PPIase activity (e.g., the upregulation or downregulation of PPIase activity (e.g., an increase or decrease in PPIase activity)) may, for example, result in a greater cis or trans content of Ser/Thr-Pro motifs present in PPIase substrates, which may affect the function of the PPIase substrate and result in the development of, e.g., cellular proliferation disorders, neurological disorders, asthma, aging-associated disorders, and tauopathies (see e.g., FIGS. 1 and 2).

Conformation-Specific Antibodies

The present invention describes methods and compositions for the generation and use of conformation-specific antibodies or fragments thereof. Conformation-specific antibodies may, for example, specifically bind to the cis or trans conformation of a polypeptide. In a specific embodiment, the conformation-specific antibody of the invention may bind to the cis or trans conformation of a phosphorylated or nonphosphorylated Xaa-Pro motif of a polypeptide (e.g., cis pT231-tau or trans pT231-tau). The Xaa-Pro motif may be a phosphorylated Ser/Thr-Pro motif of a polypeptide (e.g., a Pin1 substrate, e.g., pT231-tau). The binding of a conformation-specific antibody to its antigen (e.g., a Pin1 substrate, e.g., pT231-tau) may be useful in the treatment, diagnosis, or monitoring of a disorder or the progression of a disorder.

Methods for the preparation and use of antibodies for therapeutic purposes are described herein and, for example, in U.S. Pat. Nos. 6,054,297; 5,821,337; 6,365,157; and 6,165,464, International Application No. PCT/US2012/035473, and U.S. patent application Ser. No. 13/504,700, hereby incorporated by reference.

Antigens

Conformation-specific antibodies of the present invention may be generated using immunogenic antigens (e.g., antigenic peptides) containing, for example, a phosphorylated or nonphosphorylated Xaa-Pro motif, where Xaa is any amino acid residue (e.g., serine or threonine) fixed in a particular conformation (e.g., the cis or trans conformation) or in mixed cis and trans conformations or any other motif or amino acid sequence that is capable of cis/trans isomerization. For example, the cis or trans content of phosphorylated or nonphosphorylated Ser/Thr-Pro-containing antigenic peptides of the invention may be fixed by stereoselective synthesis of (Z)- and (E)-alkene mimics by Still-Wittig and Ireland-Claisen rearrangements (J. Org. Chem., 68: 2343-2349, 2003; hereby incorporated by reference). Alternatively, the cis or trans content of phosphorylated or nonphosphorylated Ser/Thr-Pro-containing antigenic peptides of the invention may be increased or fixed by substituting a proline amino acid residue with a proline analog. Proline analogs include, without limitation, homoproline, pipecolic acid (Pip), dimethyl proline (DMP), azetidine-2-carboxylic acid (Aze), tert-butyl-L-proline (TBP), trans-4-fluoro-L-proline (t-4F-Pro), and cis-4-fluoro-L-proline (c-4F-Pro). The cis or trans content of a given antigen may be analyzed by, for example, nuclear magnetic resonance (NMR) analysis.

Antigenic peptides of the invention may contain a phosphorylated or nonphosphorylated Xaa-Pro motif, wherein Xaa is any amino acid residue (e.g., serine or threonine), which is capable of cis/trans isomerization. The antigenic peptide may contain the amino acid residues of the Xaa-Pro motif of a Pin1 substrate (examples of which are provided in Table 1), with the proline residue substituted for a proline analog. The antigenic peptide may also contain the amino acid residues of the Xaa-Pro motif of a full-length polypeptide. The antigenic peptide may further include additional residues surrounding the Xaa-Pro motif of the full-length polypeptide. For example, the antigenic peptide may include the 3-10 amino acid residues N-terminal to the Xaa residue of a full-length polypeptide and the 3-10 amino acid residues C-terminal to the proline of a full-length polypeptide. The antigenic peptide of the invention may be, for example, at least 4, 5, 6, 7, or 8 amino acid residues in length. The antigenic peptide may be between 8 and 20 amino acid residues in length (e.g., 8, 9, 10, 11, 12, 13, 14, 15, 16, 17, 18, 19, or 20 amino acids residues in length) or may be over 20 amino acid residues in length.

Such antigens may be produced and purified by any of a variety of methods known to one of skill in the art. Antigenic peptides may be produced and purified by, e.g., solid-phase chemical synthesis, in vitro transcription/translation, or by recombinant technology. The antigenic peptides may optionally be chemically coupled to a carrier protein or the peptides may be generated as fusion proteins to increase antigenicity. Antigenic peptides may be screened based upon their ability to induce the production of conformation-specific antibodies. In this respect, such screening techniques may include, but are not limited to, enzyme-linked immunosorbant assays (ELISA), immunoprecipitation, or other immunoassays.

Exemplary antigens useful in the production of conformation-specific antibodies include antigens containing a phosphorylated or nonphosphorylated Ser/Thr-homoproline, Ser/Thr-Pip, Ser/Thr-DMP, Ser/Thr-Aze, Ser/Thr-TBP, Ser/Thr-t-4F-Pro, Ser/Thr-c-4F-Pro motif. Specific examples of such antigens include, e.g., pT668-Pip and pT668-DMP APP peptide (VDAAV-pT668-Pro-EERHLSK), pT231-Pip tau peptide, and pT231-DMP tau peptide (KVAVVR-pT231-Pro-PKSPS). Other exemplary antigens are also described in U.S. Patent Application Publication No. 2008/0058276, hereby incorporated by reference. Such peptides may be used as antigens for generating, e.g., polyclonal or monoclonal antibodies (e.g., rabbit or mouse monoclonal antibodies).

In preferred embodiments, the antigens of the invention will bind to variable regions with the following sequences:

```
Cis mAb-#113
Heavy chain CDRs
CDR1: SYWIH                      (SEQ ID NO: 1)

CDR2: VIDPSDSYTRYNQKFKG          (SEQ ID NO: 2)

CDR3: WEVDYWGQGTTLTVSS           (SEQ ID NO: 3)

Cis mAb-#113
Light chain CDRs
CDR1: RSSQSLVHSDGNTYLH           (SEQ ID NO: 4)

CDR2: KVSNRFS                    (SEQ ID NO: 5)
```

-continued

```
CDR3: SQSTHVPWT                  (SEQ ID NO: 6)

Cis mAb-#74
Heavy chain CDRs
CDR1: SGYYWN                     (SEQ ID NO: 7)

CDR2: YISYDGSNNYNPSLKN           (SEQ ID NO: 8)

CDR3: LRRDAYWGQGTLVTVSA          (SEQ ID NO: 9)

Cis mAb-#74
Light chain CDRs
CDR1: RASQDISNYLN                (SEQ ID NO: 10)

CDR2: YTSRLHS                    (SEQ ID NO: 11)

CDR3: QQGNTLPWT                  (SEQ ID NO: 12)

Trans mAb-#25
Heavy chain CDRs
CDR1: DTYMH                      (SEQ ID NO: 13)

CDR2: RIDPANGNTRYDPKFQG          (SEQ ID NO: 14)

CDR3: RVGYYFDYWGQGTTLTVSS        (SEQ ID NO: 15)

Trans mAb-#25
Light chain CDRs
CDR1: KSSQSVLYSSDLKNYLA          (SEQ ID NO: 16)

CDR2: WASTRES                    (SEQ ID NO: 17)

CDR3: HQYLSSYT                   (SEQ ID NO: 18)

Trans mAb-#69
Light chain CDRs
CDR1: KSSQSLLYTGNQKNYLA          (SEQ ID NO: 19)

CDR2: WASTRES                    (SEQ ID NO: 20)

CDR3: QQYYSYPWT                  (SEQ ID NO: 21)
```

Generation and Purification of Conformation-Specific Antibodies

The antigens of the present invention may be used to generate, for example, monoclonal, polyclonal, chimeric, humanized, or recombinant conformation-specific antibodies by any method known in the art. These methods include the immunological methods described by Kohler and Milstein (Nature 256: 495-497, 1975 and Eur. J. Immunol. 6: 511-519, 1976) and Campbell ("Monoclonal Antibody Technology, The Production and Characterization of Rodent and Human Hybridomas," in Burdon et al., Eds., Laboratory Techniques in Biochemistry and Molecular Biology, Volume 13, Elsevier Science Publishers, Amsterdam, 1985), as well as by the recombinant DNA method described by Huse et al. (Science 246: 1275-1281, 1989).

Briefly, the antigens of the present invention may, in combination with an adjuvant, be administered to a host animal (e.g., a rabbit, mouse, goat, sheep, or chicken). The administration of such antigens may be accomplished by any of a variety of methods, including, but not limited to, subcutaneous or intramuscular injection. Once administered, the results of antibody titers produced in the host animal are monitored, which may be conducted by any of a variety of techniques well-known in the art (e.g., routine bleeds), with the antisera being isolated (e.g., via centrifugation) and thereafter screened for the presence of antibodies having a binding affinity for, e.g., the cis or trans conformation of a polypeptide or polypeptide fragment. Screening for the desired antibody may be accomplished by techniques including, e.g., radioimmunoassays, ELISA, sandwich immunoassays, immunoradiometric assays, gel diffusion precipitation reactions, in situ immunoassays (e.g., using colloidal gold, enzymatic, or radioisotope labels), Western blots, precipitation reactions, agglutination assays (e.g., gel agglutination assays or hemagglutination assays), complement fixation assays, immunofluorescence assays, protein A assays, and immunoelectrophoresis assays.

The resultant antisera derived from the host animal may be affinity purified to derive the antibodies for the present invention. The antisera may be purified via conventional techniques, such as the introduction of the antisera onto a separation column. The antigens of the present invention may be immobilized on the column to isolate and purify conformation-specific antibodies. For example, an antigenic peptide containing a Ser/Thr-DMP motif that is used to generate a cis-specific antibody may be immobilized on a column and used to purify the resulting cis-specific antibody from, e.g., antibodies in the trans conformation. The column may then be washed to remove antibodies not having specificity for the antigen immobilized on the column, with the remaining conformation-specific antibody ultimately being eluted from the column. The isolated conformation-specific antibody may then be stored per conventional practices known to those skilled in the art.

Alternatively, antibody libraries (e.g., naive antibody libraries, synthetic antibody libraries, semi-synthetic antibody libraries, or combinatorial libraries) may be screened for the identification of conformation-specific antibodies. Such libraries are commercially available from a number of sources (e.g., Cambridge Antibody, Cambridge, United Kingdom, Genetastix Corporation, Pacific Northwest Laboratory, Richland, Wash., and MorphoSys AG, Munich, Germany (e.g., HuCal GOLD)). See, e.g., U.S. Pat. Nos. 6,696,248; 6,706,484; 6,828,422; and 7,264,963, hereby incorporated by reference.

Screening of an antibody library may be performed by using one of the methods known to one of skill in the art including, e.g., phage-display, selectively infective phage, polysome technology, and assay systems for enzymatic activity or protein stability. Antibodies having the desired property can be identified, for example, by sequencing of the corresponding nucleic acid sequence, by amino acid sequencing, or by mass spectrometry. Optimization is performed by replacing sub-sequences with different sequences (e.g., random sequences) and then repeating the screening step one or more times. The antibodies may be screened for, e.g., optimized affinity or specificity for a target molecule (e.g., the cis or trans conformation of a target molecule), optimized expression yields, optimized stability, or optimized solubility.

Conformation-specific antibodies of the present invention recognize and specifically bind to, for example, a particular conformation (e.g., the cis or trans conformation) of its complementary antigen. For example, as described herein, the conformation-specific antibody may specifically bind to the cis conformation of a phosphorylated or nonphosphorylated Xaa-Pro motif of a polypeptide (e.g., a Ser/Thr-Pro motif of a Pin1 substrate, e.g., pT231-tau), but will not specifically bind to the trans conformation of the phosphorylated or nonphosphorylated Xaa-Pro motif of the polypeptide. In this case, the $K_d$ between the conformation-specific antibody and its antigen is, for example, at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M or greater. In addition to the binding specificity, the conformation-specific antibody will have, for example, at least 10- to 100-fold greater affinity to one conformation (e.g., the cis conformation) than to another conformation (e.g., the trans conformation) of the Xaa-Pro motif. The conformation-specific antibody may have, for example, at least $10^3$-, $10^4$-, $10^5$-, $10^6$-, $10^7$-, $10^8$-, $10^9$-, or $10^{10}$-fold greater affinity to one conformation (e.g., the cis conformation) than another conformation (e.g., the trans conformation).

The invention also features antibodies based on several new monoclonal antibodies developed according to the methods of the invention. The sequences of these antibodies, and their complementary determining regions (CDRs), is set forth below.

```
Cis mAb-#113
Heavy chain CDRs
                                                       (SEQ ID NO: 1)
CDR1: SYWIH (SEQ ID NO: 2)
CDR2: VIDPSDSYTRYNQKFKG (SEQ ID NO: 3)
CDR3: WEVDYWGQGTTLTVSS SEQ ID NO: 22 (heavy chain full protein sequence)
MGVSLQLLGT QDLTMRWSCI ILFLVATATG VNSQVQLQQP GAELVKPGAS VKMSCKASGY

TFTSYWIHWV KQRPGQGLEW IGVIDPSDSY TRYNQKFKGK ATLTVDTSSS TAYMQLSSLT

SEDSAVYYCT TWEVDYWGQG TTLTVSSAKT TPPSVYPLAP GSL

SEQ ID NO: 29 (heavy chain full nucleic acid sequence)
ATGGGGGTCTCTCTACAGTTACTAGGCACACAGGATCTCACCATGAGATGGAGCTGTATCATCCTCTTCT

TGGTAGCAACAGCTACAGGTGTCAACTCCCAGGTCCAACTGCAGCAGCCTGGGGCTGAGCTGGTGAAGCC

TGGGGCTTCAGTGAAGATGTCCTGCAAGGCTTCTGGCTACACCTTCACCAGCTACTGGATACACTGGGTG

AAGCAGAGGCCTGGACAAGGCCTTGAGTGGATCGGAGTGATTGATCCTTCTGATAGTTATACTAGGTACA

ATCAAAAGTTCAAGGGCAAGGCCACGTTGACTGTAGACACATCCTCCAGCACAGCCTACATGCAACTCAG

CAGCCTGACATCTGAGGACTCTGCGGTCTATTACTGTACAACATGGGAGGTTGACTACTGGGGCCAAGGC

ACCACTCTCACAGTCTCCTCAGCCAAAACAACACCCCCATCAGTCTATCCCCTGGCCCCTGGAAGCTTGG

G

Cis mAb-#113
Light chain CDRs
                                                       (SEQ ID NO: 4)
CDR1: RSSQSLVHSDGNTYLH (SEQ ID NO: 5)
CDR2: KVSNRFS (SEQ ID NO: 6)
CDR3: SQSTHVPWT SEQ ID NO: 23 (light chain full protein sequence)
MGTDQSPQAV SSGCLLKMKL PVRLLVLMFW IPASNSDVVM TQTPLSLPVS LGDQASISCR

SSQSLVHSDG NTYLHWYLQK PGQSPKLLIY KVSNRFSGVP DRFSGSGSGT DFTLKISRLE

AEDLGVYFCS QSTHVPWTFG GGTKLEIKRA DAAPTVSIFP PSSKLG

SEQ ID NO: 30 (light chain full nucleic acid sequence)
ATGGGGACTGATCAGTCTCCTCAGGCTGTCTCCTCAGGTTGCCTCCTCAAAATGAAGTTGCCTGTTAGGC

TGTTGGTGCTGATGTTCTGGATTCCTGCTTCCAACAGTGATGTTGTGATGACCCAAACTCCACTCTCCCT

GCCTGTCAGTCTTGGAGATCAAGCCTCCATCTCTTGCAGATCTAGTCAGAGCCTTGTCCACAGTGATGGA

AACACCTATTTACATTGGTACCTGCAGAAGCCAGGCCAGTCTCCAAAGCTCCTGATCTACAAAGTTTCCA

ACCGATTTTCTGGGGTCCCAGACAGGTTCAGTGGCAGTGGATCAGGGACAGATTTCACACTCAAGATCAG

CAGACTGGAGGCTGAGGATCTGGGAGTTTATTTCTGCTCTCAAAGTACACATGTTCCGTGGACGTTCGGT

GGAGGCACCAAGCTGGAAATCAAACGGGCTGATGCTGCACCAACTGTATCCATCTTCCCACCATCCAGTA

AGCTTGGG
```

-continued

Cis mAb-#74
Heavy chain CDRs (SEQ ID NO: 7)
CDR1: SGYYWN (SEQ ID NO: 8)
CDR2: YISYDGSNNYNPSLKN (SEQ ID NO: 9)
CDR3: LRRDAYWGQGTLVTVSA SEQ ID NO: 24 (heavy chain full protein sequence)
MKVLSLLYLL TAIPGILSDV QLQESGPGLV KPSQSLSLTC SVTGYSITSG YYWNWIRQFP

GNKLEWMGYI SYDGSNNYNP SLKNRISITR DTSKNQFFLK LNSVTTEDTA TYYCAGLRRD

AYWGQGTLVT VSAAKTTPPS VYPLAPGSL

SEQ ID NO: 31 (heavy chain full nucleic acid sequence)
ATGAAAGTGTTGAGTCTGTTGTACCTGTTGACAGCCATTCCTGGTATCCTGTCTGATGTACAGCTTCAGG

AGTCAGGACCTGGCCTCGTGAAACCTTCTCAGTCTCTGTCTCTCACCTGCTCTGTCACTGGCTACTCCAT

CACCAGTGGTTATTACTGGAACTGGATCCGGCAGTTTCCAGGAAACAAACTGGAATGGATGGGCTACATA

AGCTACGACGGTAGCAATAACTACAACCCATCTCTCAAAAATCGAATCTCCATCACTCGTGACACATCTA

AGAACCAGTTTTTCCTGAAGTTGAATTCTGTGACTACTGAGGACACAGCTACATATTACTGTGCGGGGTT

ACGACGTGATGCTTACTGGGGCCAAGGGACTCTGGTCACTGTCTCTGCAGCCAAAACAACACCCCCATCA

GTCTATCCACTGGCCCCTGGAAGCTTGGG

Cis mAb-#74
Light chain CDRs (SEQ ID NO: 10)
CDR1: RASQDISNYLN (SEQ ID NO: 11)
CDR2: YTSRLHS (SEQ ID NO: 12)
CDR3: QQGNTLPWT SEQ ID NO: 25 (light chain full protein sequence)
MMSSAQFLGL LLLCFQGTRC DIQMTQTTSS LSASLGDRVT ISCRASQDIS NYLNWYQQKP

DGTVKLLIYY TSRLHSGVPS RFSGSGSGTD YSLTISNLEQ EDIATYFCQQ GNTLPWTFGG

GTKLEIKRAD AAPTVSIFPP SSKLG

SEQ ID NO: 32 (light chain full nucleic acid sequence)
ATGATGTCCTCTGCTCAGTTCCTTGGTCTCCTGTTGCTCTGTTTTCAAGGTACCAGATGTGATATCCAGA

TGACACAGACTACATCCTCCCTGTCTGCCTCTCTGGGAGACAGAGTCACCATCAGTTGCAGGGCAAGTCA

GGACATTAGCAATTATTTAAACTGGTATCAGCAGAAACCAGATGGAACTGTTAAACTCCTGATCTACTAC

ACATCAAGATTACACTCAGGAGTCCCATCAAGGTTCAGTGGCAGTGGGTCTGGAACAGATTATTCTCTCA

CCATTAGCAACCTGGAGCAAGAAGATATTGCCACTTACTTTTGCCAACAGGGTAATACGCTTCCGTGGAC

GTTCGGTGGAGGCACCAAGCTGGAAATCAAACGGGCTGATGCTGCACCAACTGTATCCATCTTCCCACCA

TCCAGTAAGCTTGGGG

Trans mAb-#25
Heavy chain CDRs (SEQ ID NO: 13)
CDR1: DTYMH (SEQ ID NO: 14)
CDR2: RIDPANGNTRYDPKFQG (SEQ ID NO: 15)
CDR3: RVGYYFDYWGQGTTLTVSS SEQ ID NO: 26 (heavy chain full protein sequence)
MKCSWVIFFL MAVVTGVTSE VQLQQSGAEL VKPGASVKLS CTASGFNIKD TYMHWVKQRP

EQGLEWIGRI DPANGNTRYD PKFQGKATIT SDTSSNTAYL QLSSLTSEDT AVYYCARRVG

YYFDYWGQGT TLTVSSAKTT PPSVYPLVPG SL

SEQ ID NO: 33 (heavy chain full nucleic acid sequence)
ATGAAATGCAGCTGGGTTATCTTCTTCCTGATGGCAGTGGTTACAGGGGTCACTTCAGAGGTTCAGCTGC

AGCAGTCTGGGGCAGAACTTGTGAAACCAGGGGCCTCAGTCAAGTTGTCCTGCACAGCTTCTGGCTTCAA

CATTAAAGACACCTATATGCACTGGGTGAAGCAGAGGCCTGAACAGGGCCTGGAGTGGATTGGAAGGATT

GATCCTGCGAATGGTAATACTAGATATGACCCAAAATTCCAGGGCAAGGCCACTATAACATCAGACACAT

CCTCCAACACAGCCTACCTGCAGCTCAGCAGCCTGACATCTGAGGACACTGCCGTCTATTACTGTGCTAG

GCGGGTGGGGTACTACTTTGACTACTGGGGCCAAGGCACCACTCTCACAGTCTCCTCAGCCAAAACGACA

CCCCCATCTGTCTATCCCCTGGTCCCTGGAAGCTTGGG

Trans mAb-#25
Light chain CDRs
                                                                                (SEQ ID NO: 16)
CDR1: KSSQSVLYSSDLKNYLA (SEQ ID NO: 17)
CDR2: WASTRES (SEQ ID NO: 18)
CDR3: HQYLSSYT SEQ ID NO: 27 (light chain full protein sequence)
MESQTQVFLS LLLWVSGTCG NIMMTQSPSS LAVSAGEKVT MSCKSSQSVL YSSDLKNYLA

WYQQKPGQSP TLLIYWASTR ESGVPDRFTG SGSGTDFTLT ISSVQAEDLA VYYCHQYLSS

YTFGGGTKLE IKRADAAPTV SIFPPSSK

SEQ ID NO: 34 (light chain full nucleic acid sequence)
ATGGAATCACAGACTCAGGTCTTCCTCTCCCTGCTGCTCTGGGTATCTGGTACCTGTGGGAACATTATGA

TGACACAGTCGCCATCATCTCTGGCTGTGTCTGCAGGAGAAAAGGTCACTATGAGCTGTAAGTCCAGTCA

AAGTGTTTTATACAGTTCAGATCTGAAGAACTACTTGGCCTGGTACCAGCAGAAACCAGGGCAGTCTCCT

ACACTGCTGATCTATTGGGCATCCACTAGGGAATCTGGTGTCCCTGATCGCTTCACAGGCAGTGGATCTG

GGACAGATTTTACTCTTACCATCAGCAGTGTACAAGCTGAAGACCTGGCAGTTTATTACTGTCATCAATA

CCTCTCCTCGTACACGTTCGGAGGGGGGACCAAGCTGGAAATAAAACGGGCTGATGCTGCACCAACTGTA

TCCATCTTCCCACCATCCAGTAAGC

Trans mAb-#69
Light chain CDRs
                                                                                (SEQ ID NO: 19)
CDR1: KSSQSLLYTGNQKNYLA (SEQ ID NO: 20)
CDR2: WASTRES (SEQ ID NO: 21)
CDR3: QQYYSYPWT SEQ ID NO: 28 (light chain full protein sequence)
MDSQAQVLML LLLWVSGTCG DIVMSQSPSS LAVSVGEKVT MSCKSSQSLL YTGNQKNYLA

WYQQKPGQSP KLLIYWASTR ESGVPDRFTG SGSGTDFTLT ISSVKAEDLA VYYCQQYYSY

PWTFGGGTKL EIKRADAAPT VSIFPPSSKL G

SEQ ID NO: 35: (light chain full nucleic acid sequence)
ATGGATTCACAGGCCCAGGTTCTTATGTTACTGCTGCTATGGGTATCTGGTACCTGTGGGGACATTGTGA

TGTCACAATCTCCATCCTCCCTAGCTGTGTCAGTTGGAGAGAAGGTTACTATGAGCTGCAAGTCCAGTCA

GAGCCTTTTATATACTGGCAATCAAAAGAACTACTTGGCCTGGTACCAGCAGAAACCAGGGCAGTCTCCT

AAACTGCTGATTTACTGGGCATCCACTAGGGAATCTGGGGTCCCTGATCGCTTCACAGGCAGTGGATCTG

```
GGACAGATTTCACTCTCACCATCAGCAGTGTGAAGGCTGAAGACCTGGCAGTTTATTACTGTCAGCAATA

TTATAGCTATCCGTGGACGTTCGGTGGAGGCACCAAGCTGGAAATCAAACGGGCTGATGCTGCACCAACT

GTATCCATCTTCCCACCATCCAGTAAGCTTGGG
```

Thus the invention features the use of the trans or cis specific antibodies listed above (or antibodies derived therefrom), in the diagnostic and therapeutic methods of the invention. For example the invention features monoclonal (e.g., humanized or human antibodies) having one, two, or three of the CDRs of either the heavy or light chain (or both) of each of the antibodies above. These CDRs can be incorporated into framework regions (e.g., human frameworks) as described herein. Furthermore, these CDRs can be varied (e.g., contain 1, 2, 3, 4, 5, or more) amino acid substitutions. Such variants can have substitutions (either exemplary or preferred) as indicated in Table 2 below:

TABLE 2

Amino acid substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; | Phe; Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; | Leu |

Figure 8:
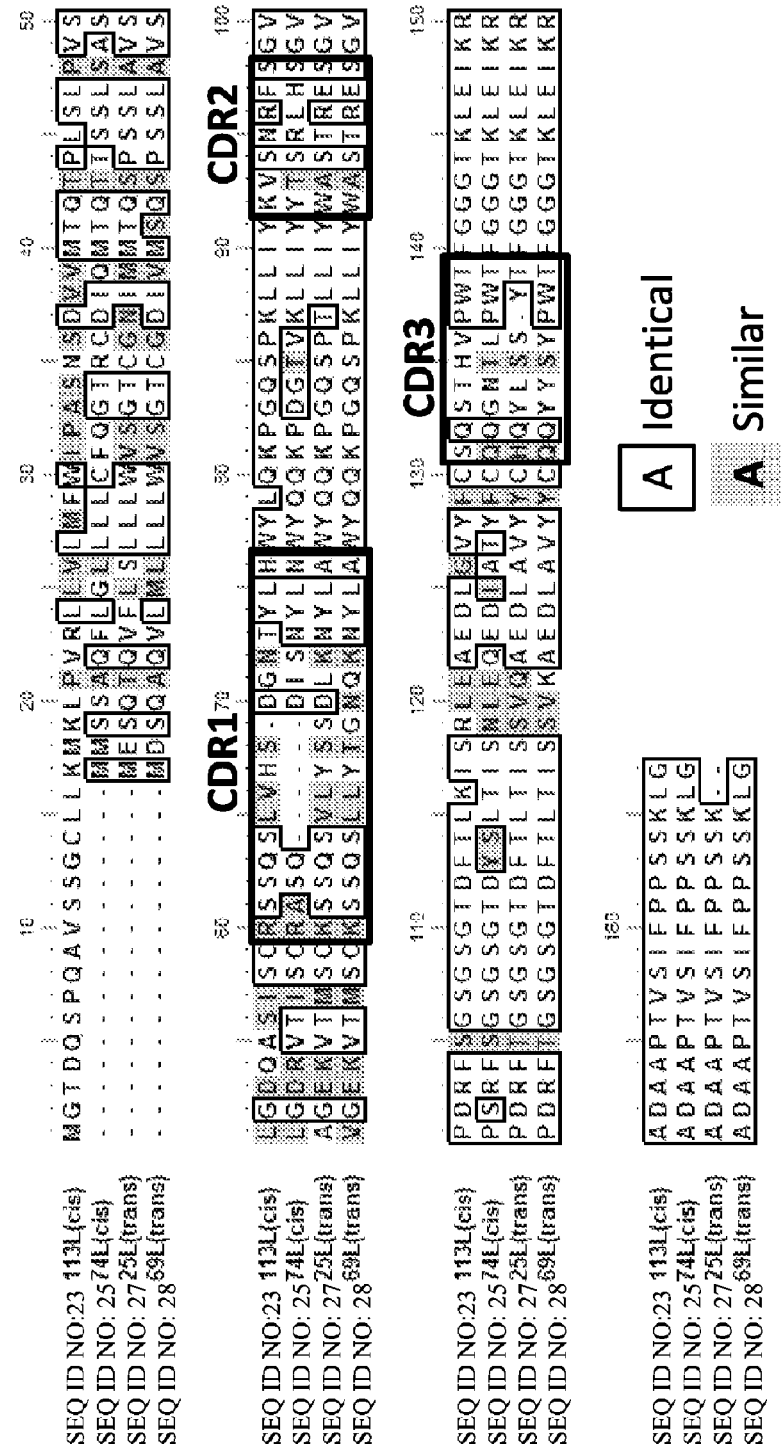
FIG. 8 shows an alignment of the light chains of the two cis mAbs (#113, #74) (SEQ ID NOs: 23 and 25, respectively) and two trans mAbs (#25, #69) (SEQ ID NOs: 27 and 28, respectively) generated from experiments where mice are immunized with 74% cis pT231-Pip tau peptide as described previously in Nakamura et al., Cell 149: 232-244, 2012. CDR 1-3 are indicated with boxes labeled CDR 1-3. Shaded boxes indicate similar residues and open boxes indicate identical residues.
Figure 9:
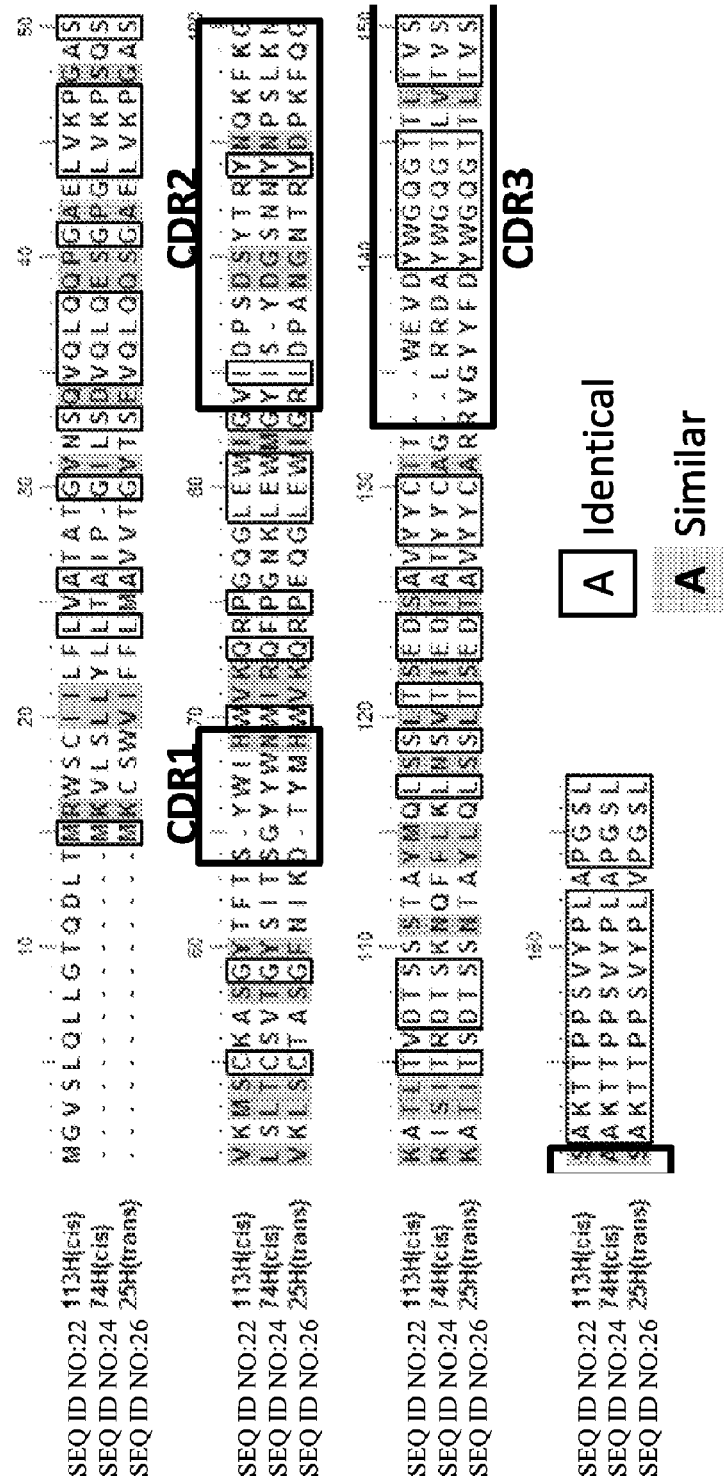
FIG. 9 shows an alignment of the heavy chains of the two cis mAbs (#113, #74) (SEQ ID NOs: 22 and 24, respectively) and one trans mAb (#25) (SEQ ID NO:26) generated from experiments where mice are immunized with 74% cis pT231-Pip tau peptide as described previously in Nakamura et al., Cell 149: 232-244, 2012. CDR 1-3 are indicated with boxes labeled CDR 1-3. Shaded boxes indicate similar residues and open boxes indicate identical residues.

Additionally, or alternatively, the variants can contain substitutions as indicated in FIGS. 8 and 9. Such variants would preferably retain residues conserved between the depicted antibodies while have changes in residues shown to vary between antibodies (e.g., the residue can be substituted according to the table above or with an alternative residue depicted in the figures). Variants may also include combinations of the CDRs of the heavy chain and light chain. For example, variants can include: CDRs 1 and 3 of the heavy chain and CDRs 1 and 3 or CDRs 1 and 2, or CDRs 2 and 3 of the light chain; CDRs 1 and 2 of the heavy chain and CDRs 1 and 3 or CDRs 1 and 2, or CDRs 2 and 3 of the light chain; CDRs 2 and 3 of the heavy chain and CDRs 1 and 3 or CDRs 1 and 2, or CDRs 2 and 3 of the light chain; CDRs 1 and 3 of the light chain and CDRs 1 and 3 or CDRs 1 and 2, and/or CDRs 2 and 3 of the heavy chain; CDRs 1 and 2 of the light chain and CDRs 1 and 3 or CDRs 1 and 2, or CDRs 2 and 3 of the heavy chain; CDRs 2 and 3 of the light chain and CDRs 1 and 3 or CDRs 1 and 2, or CDRs 2 and 3 of the heavy chain, or combinations thereof. In all cases, variants of the above antibodies will retain their ability to specifically bind a cis (or trans) conformation of the pTau epitope as described herein.

Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature 321:522-5, 1986; Riechmann et al., Nature 332:323-7, 1988; Verhoeyen et al., Science 239:1534-6, 1988), by substituting hypervariable region sequences for the corresponding sequences of a human antibody. Accordingly, such "humanized" antibodies are chimeric antibodies (U.S. Pat. No. 4,816,567), where substantially less than an intact human variable domain has been substituted by the corresponding sequence from a non-human species. In practice, humanized antibodies are typically human antibodies in which at least some hypervariable region residues as well as other variable region residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al., J. Immunol. 151:2296-308, 1993; Chothia et al., J. Mol. Biol. 196:901-17, 1987. Another method uses a particular framework derived from the consensus sequence of all human antibodies of a particular subgroup of light or heavy chains. The same framework may be used for several different humanized antibodies. See, e.g., Carter et al., Proc. Natl. Acad. Sci. USA 89:4285-9, 1992; Presta et al., J. Immunol. 151:2623-32, 1993.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human antibodies of the invention can be constructed by combining Fv clone variable domain sequence(s) selected from human-derived phage display libraries with known human constant domain sequences(s) (Hoogenboom et al., *J. Mol. Biol.* 227:381-8, 1992; Marks et al., *J. Mol. Biol.* 222:581-97, 1991). Alternatively, human monoclonal antibodies of the invention can be made by the hybridoma method. Human myeloma and mouse-human heteromyeloma cell lines for the production of human monoclonal antibodies have been described, for example, by Kozbor, *J. Immunol.* 133:3001-5, 1984; Brodeur et al., *Monoclonal Antibody Production Techniques and Applications*, pp. 51-63 (Marcel Dekker, Inc., New York, 1987); and Boerner et al., *J. Immunol.* 147: 86-95, 1991.

It is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA* 90:2551-5, 1993; Jakobovits et al., *Nature* 362:255-8, 1993; Brüggemann et al., *Year Immunol.* 7:33-40, 1993.

Gene shuffling can also be used to derive human antibodies from non-human, e.g., rodent, antibodies, where the human antibody has similar affinities and specificities to the starting non-human antibody. According to this method, which is also called "epitope imprinting," either the heavy or light chain variable-region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab where the human chain restores the antigen binding site destroyed upon removal of the corresponding non-human chain in the primary phage display clone, i.e., the epitope governs (imprints) the choice of the human chain partner. When the process is repeated in order to replace the remaining non-human chain, a human antibody is obtained (see PCT Publication WO 93/06213). Unlike traditional humanization of non-human antibodies by CDR grafting, this technique provides completely human antibodies, which have no FR or CDR residues of non-human origin.

Antibody Fragments

The invention also features antibody fragments that comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

Fv is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs) of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

Single-chain Fv or scFv antibody fragments comprise the $V_H$ and $V_L$ domains of antibody, where these domains are present in a single polypeptide chain. Generally, the scFv polypeptide further comprises a polypeptide linker between the $V_H$ and $V_L$ domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

Diabodies are antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, European Patent No. 404,097; PCT Publication WO 1993/01161; Hudson et al., *Nat. Med.* 9:129-34, 2003; and Hollinger et al., *Proc. Natl. Acad. Sci. USA* 90:6444-8, 1993. Triabodies and tetrabodies are also described in Hudson et al., *Nat. Med.* 9:129-34, 2003.

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. *Nat. Med.* 9:129-134, 2003.

Various techniques have been developed for the production of antibody fragments. Traditionally, these fragments were derived via proteolytic digestion of intact antibodies (see, e.g., Morimoto et al., *J. Biochem. Biophys. Methods*

24:107-17, 1992; and Brennan et al., *Science* 229:81-3, 1985). However, these fragments can now be produced directly by recombinant host cells. Fab, Fv, and ScFv antibody fragments can all be expressed in and secreted from *E. coli*, thus allowing the facile production of large amounts of these fragments. Antibody fragments can be isolated from the antibody phage libraries. Alternatively, Fab'-SH fragments can be directly recovered from *E. coli* and chemically coupled to form F(ab')$_2$ fragments (Carter et al., *Bio/Technology* 10:163-7, 1992). In another approach, F(ab')$_2$ fragments are isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner.

Therapeutic Formulations

The conformation-specific antibodies of the present invention may be used in the treatment, inhibition, or prevention of a tauopathy, TBI, or stroke. The conformation-specific antibodies may also be used to ameliorate symptoms of a tauopathy, TBI, or stroke.

The conformation-specific antibodies of the present invention can be formulated and administered in a variety of ways (e.g., routes known for specific indications, including, but not limited to, topically, orally, subcutaneously, bronchial injection, intravenously, intracerebrally, intranasally, transdermally, intraperitoneally, intramuscularly, intrapulmonary, vaginally, rectally, intraarterially, intralesionally, parenterally, intraventricularly in the brain, or intraocularly). For example, the pharmaceutical composition containing the conformation-specific antibody may be in the form of a pill, tablet, capsule, liquid, or sustained-release tablet for oral administration; a liquid for intravenous or subcutaneous administration; a polymer or other sustained-release vehicle for local administration; or an ointment, cream, gel, liquid, or patch for topical administration.

Continuous systemic infusion or periodic injection of the conformation-specific antibody can be used to treat or prevent a tauopathy, TBI, or stroke. Treatment can be continued for a period of time ranging from one day through the lifetime of the subject, for example, 1 to 100 days, 1 to 60 days, or until the symptoms of the disorder are reduced or removed. Dosages vary depending on the severity of the disorder or symptoms of the disorder. Sustained-release systems and semipermeable, implantable membrane devices are also useful as a means for delivering the pharmaceutical composition of the invention. In another embodiment, the composition is administered locally, e.g., by inhalation, and this administration can be repeated periodically.

Therapeutic formulations are prepared using standard methods known in the art by mixing the active ingredient having the desired degree of purity with optional physiologically acceptable carriers, excipients, or stabilizers in the form of lyophilized formulations or aqueous solutions (see, e.g., Remington's Pharmaceutical Sciences, 20$^{th}$ edition, Ed. A. Gennaro, 2000, Lippincott, Williams & Wilkins, Philadelphia, Pa.). Acceptable carriers include, e.g., saline; buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagines, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at physiological concentrations. Optionally, the formulations of the invention can contain a pharmaceutically acceptable preservative. In some embodiments, the preservative concentration ranges from 0.1 to 2.0% v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant. Preferred surfactants are non-ionic detergents. Preferred surfactants include Tween-20 and pluronic acid (F68). Suitable surfactant concentrations are, e.g., 0.005 to 0.02%.

The conformation-specific antibodies of the invention are administered to the subject in therapeutically effective amounts. Preferably, the antibodies are administered parenterally or intravenously by continuous infusion. The dose and dosage regimen depends upon the severity of the disorder and the overall health of the subject. The amount of antibody administered is typically in the range of about 0.001 to about 10 mg/kg of subject weight, preferably 0.01 to about 5 mg/kg of subject weight.

For parenteral administration, the conformation-specific antibodies are formulated in a unit dosage injectable form (e.g., solution, suspension, or emulsion) in association with a pharmaceutically acceptable parenteral vehicle. Such vehicles are inherently non-toxic and non-therapeutic. Examples of such vehicles include, e.g., water, saline, Ringer's solution, dextrose solution, and 5% human serum albumin. Nonaqueous vehicles, such as fixed oils and ethyl oleate, may also be used. Liposomes may be used as carriers. The vehicle may contain minor amounts of additives, such as substances that enhance isotonicity and chemical stability (e.g., buffers and preservatives). The antibodies typically are formulated in such vehicles at concentrations of about 1 mg/ml to 10 mg/ml.

The dosage required depends on the choice of the route of administration; the nature of the formulation; the nature of the subject's disorder; the subject's size, weight, surface area, age, and sex; other drugs being administered; and the judgment of the subject's physician. Wide variations in the needed dosage are to be expected in view of the variety of polypeptides and fragments available and the differing efficiencies of various routes of administration. For example, oral administration would be expected to require higher dosages than administration by intravenous injection. Variations in these dosage levels can be adjusted using standard empirical routines for optimization, as is well understood in the art. Administrations can be single or multiple (e.g., 2-, 3-, 6-, 8-, 10-, 20-, 50-, 100-, 150-, or more administrations). The composition can be administered at anytime (e.g., after diagnosis or detection of a disorder or a condition associated with the disorder (e.g., using the diagnostic methods known in the art or described herein) or before diagnosis of a disorder to a subject at risk of developing the disorder). Encapsulation of the antibody in a suitable delivery vehicle (e.g., polymeric microparticles or implantable devices) may increase the efficiency of delivery, particularly for oral delivery.

Where sustained release administration of the conformation-specific antibody is desired in a formulation with release characteristics suitable for the treatment of any disorder requiring administration of the antibody, microencapsulation of the antibody may be contemplated. Microencapsulation of polypeptides for sustained release has been successfully performed with human growth hormone (rhGH), interferon- (rhIFN-), interleukin-2, and MN rgp120 (see, e.g., Johnson et al., Nat. Med. 2: 795-799, 1996; Yasuda, Biomed. Ther. 27: 1221-1223, 1993; Hora et al., Bio/Technology 8: 755-758 1990; Cleland, "Design and Production of Single Immunization Vaccines Using Polylactide Polyglycolide Microsphere Systems," in "Vaccine Design: The Subunit and Adjuvant Approach," Powell and Newman, Eds., Plenum Press: New York, pp. 439-462, 1995; WO 97/03692; WO 96/40072; WO 96/07399; and U.S. Pat. No. 5,654,010, hereby incorporated by reference).

The sustained-release formulations may include those developed using poly-lactic-coglycolic acid (PLGA) polymer. The degradation products of PLGA, lactic and glycolic acids, can be cleared quickly from the human body. Moreover, the degradability of this polymer can be adjusted from months to years depending on its molecular weight and composition (see, e.g., Lewis, "Controlled release of bioactive agents from lactide/glycolide polymer," in M. Chasin and Dr. Langer (Eds.), Biodegradable Polymers as Drug Delivery Systems (Marcel Dekker: New York, pp. 1-41, 1990).

The antibody for use in the present invention may also be modified in a way to form a chimeric molecule comprising a conformation-specific antibody fused to another heterologous polypeptide or amino acid sequence, such as an Fc sequence or an additional therapeutic molecule (e.g., a chemotherapeutic agent).

The conformation-specific antibody of the present invention may be packaged alone or in combination with other therapeutic compounds as a kit. Non-limiting examples include, e.g., kits that contain, e.g., one pill, two pills, a powder (optionally in combination with a pill or tablet), a suppository and a liquid in a vial, or two topical creams. The kit can include optional components that aid in the administration of the unit dose to patients, such as vials for reconstituting powder forms, syringes for injection, customized IV delivery systems, or inhalers. Additionally, the unit dose kit can contain instructions for preparation and administration of the compositions. The kit may be manufactured as a single-use unit dose for one subject, multiple doses for a particular subject (e.g., at a constant dose or in which the individual compounds may vary in potency as therapy progresses), or the kit may contain multiple doses suitable for administration to multiple subjects (e.g., "bulk packaging"). The kit components may be assembled in cartons, blister packs, bottles, tubes, or vials.

Indications

The antibodies of the invention are useful for the treatment of disorders characterized by pathologically high levels of either the cis or trans conformation of, e.g., p-Tau. Such treatment can be used in patients identified as having pathologically high levels of either the cis or trans conformation of, e.g., p-Tau (e.g., those diagnosed by the methods described herein) or in patients diagnosed with a disease known to be associated with such pathological levels. Such disorders include neurological disorders, e.g., Alzheimer's disease (AD), mild cognitive impairment (MCI), Parkinson's disease (PD), multiple sclerosis (MS), muscular dystrophy, corticobasal degeneration, dementia pugilistica, Down's syndrome, frontotemporal dementias, myotonic dystrophy, Niemann-Pick disease, Pick's disease, prion disease, progressive supranuclear palsy, subacute sclerosing panencephalitis, convulsive disorders (e.g., epilepsy), vascular dementia, age-related dementia, head trauma, stroke, neurofibromatosis, Lewy body disease, amyotrophic lateral sclerosis (ALS), peripheral neuropathies, and macular degeneration. Other disorders that can be treated by the antibodies of the invention include: traumatic brain injury (TBI), chronic traumatic encephalopathy (CTE), progressive supranuclear palsy, frontotemporal lobar degeneration, Lytico-Bodig disease, tangle-predominant dementia, meningioangiomatosis, subacute sclerosing panencephalitis.

Diagnostics

The present invention features methods and compositions to treat, diagnose, and monitor the progression of a disorder described herein (e.g., a tauopathy, TBI, or stroke). The methods and compositions can include the detection and measurement of, for example, Pin1 substrates (or any fragments or derivatives thereof, e.g., pT231-tau) containing a phosphorylated Ser/Thr-Pro motif in a cis or trans conformation (e.g., cis pT231-tau and/or trans pT231-tau). The methods can include measurement of absolute levels of the pT231-tau in a cis or trans conformation as compared to a normal reference. For example, a serum level of pT231-tau in the cis or trans conformation that is less than 5 ng/ml, 4 ng/ml, 3 ng/ml, 2 ng/ml, or less than 1 ng/ml serum is considered to be predictive of a good outcome in a patient diagnosed with a disorder (e.g., a tauopathy). A serum level of the substrate in the cis or trans conformation that is greater than 5 ng/ml, 10 ng/ml, 20 ng/ml, 30 ng/ml, 40 ng/ml, or 50 ng/ml is considered diagnostic of a poor outcome in a subject already diagnosed with a disorder.

For diagnoses based on relative levels of substrate in a particular conformation (e.g., a pT231-tau in the cis or trans conformation), a subject with a disorder (e.g., a taupathy) will show an alteration (e.g., an increase of 10%, 20%, 30%, 40%, 50%, 60%, 70%, 80%, 90%, or more) in the amount of the substrate in, for example, the cis conformation or an alteration in the ratio between the cis and trans conformation. A normal reference sample can be, for example, a prior sample taken from the same subject prior to the development of the disorder or of symptoms suggestive of the disorder, a sample from a subject not having the disorder, a sample from a subject not having symptoms of the disorder, or a sample of a purified reference polypeptide in a given conformation at a known normal concentration (i.e., not indicative of the disorder).

The invention also features the early diagnosis or predisposition of a subject to a mild cognitive impairment (MCI) a tauopathy (e.g., AD, CTE), or TBI. The methods and compositions include detection and measurement of cis pT231-tau and the cis:trans pT231-tau ratio. An elevated level of cis pT231 or cis:trans ratio would indicate a subject is at risk of AD and such a subject population would benefit from a cis pT231-tau-targeted immunotherapy described herein. The early diagnostic and monitoring methods of the invention are also useful in assessing a patient's therapeutic response in potential clinical trials. A cis:trans pT231-tau ratio decrease would indicate that the therapy is effective in targeting MCI, a tauopathy (e.g., AD, CTE), or TBI. Such early diagnosis can be performed before any symptoms of the neurological disorder have been presented (e.g., in patients known or suspected to have brain trauma (e.g., repeated brain trauma) or a family history of neurological diseases.

Standard methods may be used to measure levels of the substrate in any bodily fluid, including, but not limited to, urine, blood, serum, plasma, saliva, amniotic fluid, or cerebrospinal fluid (CSF). Such methods include immunoassay, ELISA, Western blotting, and quantitative enzyme immunoassay techniques.

For diagnostic purposes, the conformation-specific antibodies may be labeled. Labeling of the antibody is intended to encompass direct labeling of the antibody by coupling (e.g., physically linking) a detectable substance to the antibody, as well as indirect labeling the antibody by reacting the antibody with another reagent that is directly labeled. For example, the antibody can be labeled with a radioactive or fluorescent marker whose presence and location in a subject can be detected by standard imaging techniques.

The diagnostic methods described herein can be used individually or in combination with any other diagnostic method described herein for a more accurate diagnosis of the presence or severity of a disorder (e.g., a tauopathy). Examples of additional methods for diagnosing such disorders include, e.g., determining the levels of other biomarkers (e.g., CSF t-tau, pT181-tau, Aβ42, or ApoE4), examining a subject's health history, immunohistochemical staining of tissues, computed tomography (CT) scans, or culture growths.

Diagnostic Kits

The invention also provides for a diagnostic test kit. For example, a diagnostic test kit can include polypeptides (e.g., conformation-specific antibodies that specifically bind to cis pT231-tau or trans pT231-tau, fragments thereof) and components for detecting and/or evaluating binding between the polypeptide (e.g., antibody) and p-Tau. Alternatively, the kit can include a cis pT231-tau or trans pT231-tau polypeptide or cis pT231-tau or trans pT231-tau fragment for the detection of cis pT231-tau or trans pT231-tau present in the serum, blood, or CSF of a subject sample. In another example, diagnostic kits of the invention may be used to identify an alteration in the level of cis pT231-tau or trans pT231-tau polypeptide relative to a reference, such as the level present in a normal control. Such a kit may include a reference sample or standard curve indicative of a positive reference or a normal control reference.

For detection, either the antibody or the cis pT231-tau or trans pT231 polypeptide is labeled, and either the antibody or the cis pT231-tau or trans pT231 polypeptide is substrate-bound, such that the polypeptide-antibody interaction can be established by determining the amount of label attached to the substrate following binding between the antibody and the cis pT231-tau or trans pT231 polypeptide. Conventional immunoassays (e.g., ELISA) may be used for detecting antibody-substrate interactions and can be provided with the kit of the invention. The polypeptides of the invention can be detected in a biological sample, such as blood, plasma, CSF, or serum.

The diagnostic kit may include instructions for the use of the kit. In one example, the kit contains instructions for the use of the kit for the diagnosis of a tauopathy (e.g., AD, CTE), TBI, and/or MCI, or a risk of developing the same. In yet another example, the kit contains instructions for the use of the kit to monitor therapeutic treatment, dosage regimens, or subjects at risk of developing a tauopathy (e.g., AD, CTE), TBI, and/or MCI.

Subject Monitoring

The diagnostic methods described herein can also be used to monitor the progression of a disorder (e.g., MCI, TBI, a tauopathy, e.g., AD, CTE) during therapy or to determine the dosages of therapeutic compounds. In one embodiment, the levels of, for example, polypeptides (e.g., pT231-tau) with pSer/Thr-Pro motifs in the cis or trans conformation are measured repeatedly as a method of diagnosing the disorder and monitoring the treatment or management of the disorder.

In order to monitor the progression of the disorder in a subject, subject samples can be obtained at several time points and may then be compared. For example, the diagnostic methods can be used to monitor subjects during before, during, and after treatment. In this example, the level of pT231-tau in the cis conformation in a subject is closely monitored using the conformation-specific antibodies of the invention and, if the level of pT231-tau in the cis conformation begins to decrease during therapy, the therapeutic regimen for treatment of the disorder can be modified as determined by the clinician (e.g., the dosage of the therapy may be changed or a different therapeutic may be administered). The monitoring methods of the invention may also be used, for example, in assessing the efficacy of a particular drug or therapy in a subject, determining dosages, or in assessing progression, status, or stage of the infection.

EXAMPLES

Example 1

Figures 3A, 3B, 3C, 3D, 3E:
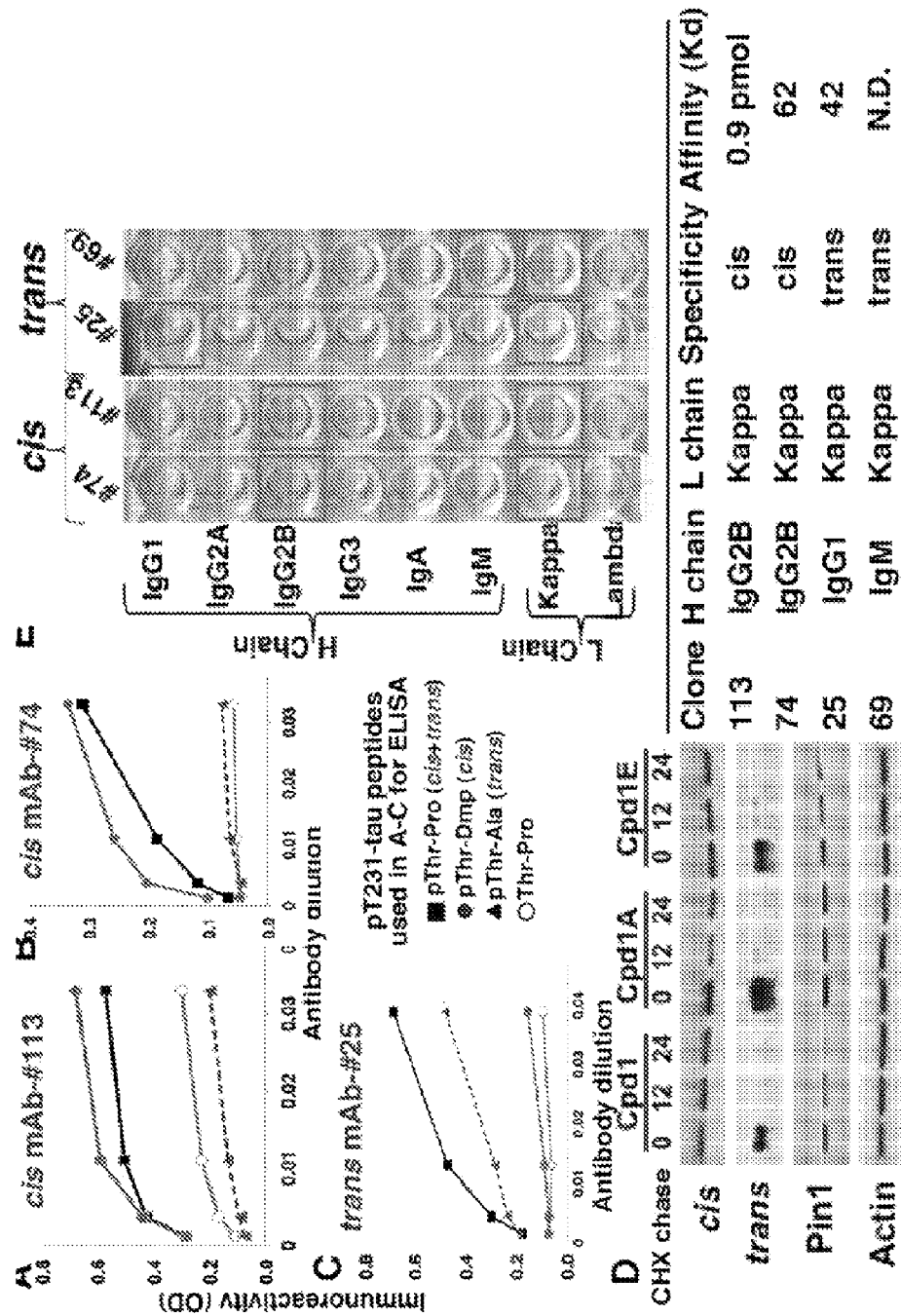
FIGS. 3A-3E show data relating to the development of cis and trans pT231-tau mouse monoclonal antibodies (mAbs). Two hybridoma clones each of the cis (FIGS. 3A, 3B) and trans (FIG. 3C) pT231-tau mouse mAbs were obtained using a pT231-Pip tau peptide as an antigen to immunize mice.

Generation of Cis and Trans pT231-tau Mouse Monoclonal Antibodies (mAbs) and Determination of their DNA Sequences To develop cis and trans pT231-tau mouse mAbs, 74% cis pT231-Pip tau peptide as described previously in Nakamura et al., *Cell* 149: 232-244, 2012 was used to immunize mice. The procedure produced 480 hybridoma clones that were then characterized. Out of the first 96 hybridoma culture supernatants screened by ELISA using pT231-tau peptides that were wild-type cis+trans (pT231-Pro), locked in cis (pT231-Dmp) or trans (pT231-Ala) or non-phosphorylated (T231-Pro), described in Nakamura et al., *Cell* 149: 232-244, 2012, two cis hybridoma clones, #113 and #74 were identified which recognized wild-type and cis pT231-tau peptides, but neither trans nor non-phosphorylated one (FIGS. 3A, 3B), and two trans hybridoma clones, #25 and #69 were identified, which recognized wild-type and trans pT231-tau peptides, but neither cis nor non-phosphorylated one (FIG. 3C). The nucleic acid and protein sequences including the CDRs of the mAb heavy chain and light chain are shown below. Moreover, cis was stable and trans was decreased as detected by cis mAb-#113 and trans mAb-#25, respectively, in cells treated with Pin1 inhibitors, Cpd1 and less active 1E, with inactive Cpd1A as a control (FIG. 3D). FIG. 3E shows the IgG subclass of the mAbs as determined using the isotyping ELISA kit (Eagle). The DNA sequences of the heavy and light chains of the mAbs were determined using 5' RACE RT-PCR techniques, as described in Bradbury et al., *Neurobiol Aging* 16:465-475, 1995. BLAST search showed that these four mAb clones are completely novel. Predicted protein sequences are highly conserved in Framework regions, with clear differences in complementary determining region (CDR) 1-3 (FIGS. 8 and 9). Notably, the two cis mAb clones contained some conserved residues that are not present in the two trans mAbs and vice versa (FIGS. 8 and 9).

Cis mAb-#113
Heavy chain CDRs

CDR1: SYWIH (SEQ ID NO: 1)

CDR2: VIDPSDSYTRYNQKFKG (SEQ ID NO: 2)

CDR3: WEVDYWGQGTTLTVSS (SEQ ID NO: 3)

SEQ ID NO: 22 (heavy chain full protein sequence)
MGVSLQLLGT QDLTMRWSCI ILFLVATATG VNSQVQLQQP GAELVKPGAS VKMSCKASGY

TFTSYWIHWV KQRPGQGLEW IGVIDPSDSY TRYNQKFKGK ATLTVDTSSS TAYMQLSSLT

SEDSAVYYCT TWEVDYWGQG TTLTVSSAKT TPPSVYPLAP GSL

SEQ ID NO: 29 (heavy chain full nucleic acid sequence)
ATGGGGGTCTCTCTACAGTTACTAGGCACACAGGATCTCACCATGAGATGGAGCTGTATCATCCTCTTCT

TGGTAGCAACAGCTACAGGTGTCAACTCCCAGGTCCAACTGCAGCAGCCTGGGGCTGAGCTGGTGAAGCC

TGGGGCTTCAGTGAAGATGTCCTGCAAGGCTTCTGGCTACACCTTCACCAGCTACTGGATACACTGGGTG

AAGCAGAGGCCTGGACAAGGCCTTGAGTGGATCGGAGTGATTGATCCTTCTGATAGTTATACTAGGTACA

ATCAAAAGTTCAAGGGCAAGGCCACGTTGACTGTAGACACATCCTCCAGCACAGCCTACATGCAACTCAG

CAGCCTGACATCTGAGGACTCTGCGGTCTATTACTGTACAACATGGGAGGTTGACTACTGGGGCCAAGGC

ACCACTCTCACAGTCTCCTCAGCCAAAACAACACCCCCATCAGTCTATCCCCTGGCCCCTGGAAGCTTGG

G

Cis mAb-#113
Light chain CDRs

CDR1: RSSQSLVHSDGNTYLH (SEQ ID NO: 4)

CDR2: KVSNRFS (SEQ ID NO: 5)

CDR3: SQSTHVPWT (SEQ ID NO: 6)

SEQ ID NO: 23 (light chain full protein sequence)
MGTDQSPQAV SSGCLLKMKL PVRLLVLMFW IPASNSDVVM TQTPLSLPVS LGDQASISCR

SSQSLVHSDG NTYLHWYLQK PGQSPKLLIY KVSNRFSGVP DRFSGSGSGT DFTLKISRLE

AEDLGVYFCS QSTHVPWTFG GGTKLEIKRA DAAPTVSIFP PSSKLG

SEQ ID NO: 30 (light chain full nucleic acid sequence)
ATGGGGACTGATCAGTCTCCTCAGGCTGTCTCCTCAGGTTGCCTCCTCAAAATGAAGTTGCCTGTTAGGC

TGTTGGTGCTGATGTTCTGGATTCCTGCTTCCAACAGTGATGTTGTGATGACCCAAACTCCACTCTCCCT

GCCTGTCAGTCTTGGAGATCAAGCCTCCATCTCTTGCAGATCTAGTCAGAGCCTTGTCCACAGTGATGGA

AACACCTATTTACATTGGTACCTGCAGAAGCCAGGCCAGTCTCCAAAGCTCCTGATCTACAAAGTTTCCA

ACCGATTTTCTGGGGTCCCAGACAGGTTCAGTGGCAGTGGATCAGGGACAGATTTCACACTCAAGATCAG

CAGACTGGAGGCTGAGGATCTGGGAGTTTATTTCTGCTCTCAAAGTACACATGTTCCGTGGACGTTCGGT

GGAGGCACCAAGCTGGAAATCAAACGGGCTGATGCTGCACCAACTGTATCCATCTTCCCACCATCCAGTA

AGCTTGGG

Cis mAb-#74
Heavy chain CDRs

CDR1: SGYYWN (SEQ ID NO: 7)

CDR2: YISYDGSNNYNPSLKN (SEQ ID NO: 8)

CDR3: LRRDAYWGQGTLVTVSA (SEQ ID NO: 9)

SEQ ID NO: 24 (heavy chain full protein sequence)
MKVLSLLYLL TAIPGILSDV QLQESGPGLV KPSQSLSLTC SVTGYSITSG YYWNWIRQFP

GNKLEWMGYI SYDGSNNYNP SLKNRISITR DTSKNQFFLK LNSVTTEDTA TYYCAGLRRD

AYWGQGTLVT VSAAKTTPPS VYPLAPGSL

SEQ ID NO: 31 (heavy chain full nucleic acid sequence)
ATGAAAGTGTTGAGTCTGTTGTACCTGTTGACAGCCATTCCTGGTATCCTGTCTGATGTACAGCTTCAGG

AGTCAGGACCTGGCCTCGTGAAACCTTCTCAGTCTCTGTCTCTCACCTGCTCTGTCACTGGCTACTCCAT

CACCAGTGGTTATTACTGGAACTGGATCCGGCAGTTTCCAGGAAACAAACTGGAATGGATGGGCTACATA

AGCTACGACGGTAGCAATAACTACAACCCATCTCTCAAAAATCGAATCTCCATCACTCGTGACACATCTA

AGAACCAGTTTTTCCTGAAGTTGAATTCTGTGACTACTGAGGACACAGCTACATATTACTGTGCGGGGTT

ACGACGTGATGCTTACTGGGGCCAAGGGACTCTGGTCACTGTCTCTGCAGCCAAAACAACACCCCCATCA

GTCTATCCACTGGCCCCTGGAAGCTTGGG

Cis mAb-#74
Light chain CDRs
                                                        (SEQ ID NO: 10)
CDR1: RASQDISNYLN (SEQ ID NO: 11)
CDR2: YTSRLHS (SEQ ID NO: 12)
CDR3: QQGNTLPWT SEQ ID NO: 25 (light chain full protein sequence)
MMSSAQFLGL LLLCFQGTRC DIQMTQTTSS LSASLGDRVT ISCRASQDIS NYLNWYQQKP

DGTVKLLIYY TSRLHSGVPS RFSGSGSGTD YSLTISNLEQ EDIATYFCQQ GNTLPWTFGG

GTKLEIKRAD AAPTVSIFPP SSKLG

SEQ ID NO: 32 (light chain full nucleic acid sequence)
ATGATGTCCTCTGCTCAGTTCCTTGGTCTCCTGTTGCTCTGTTTTCAAGGTACCAGATGTGATATCCAGA

TGACACAGACTACATCCTCCCTGTCTGCCTCTCTGGGAGACAGAGTCACCATCAGTTGCAGGGCAAGTCA

GGACATTAGCAATTATTTAAACTGGTATCAGCAGAAACCAGATGGAACTGTTAAACTCCTGATCTACTAC

ACATCAAGATTACACTCAGGAGTCCCATCAAGGTTCAGTGGCAGTGGGTCTGGAACAGATTATTCTCTCA

CCATTAGCAACCTGGAGCAAGAAGATATTGCCACTTACTTTTGCCAACAGGGTAATACGCTTCCGTGGAC

GTTCGGTGGAGGCACCAAGCTGGAAATCAAACGGGCTGATGCTGCACCAACTGTATCCATCTTCCCACCA

TCCAGTAAGCTTGGGG

Trans mAb-#25
Heavy chain CDRs
                                                        (SEQ ID NO: 13)
CDR1: DTYMH (SEQ ID NO: 14)
CDR2: RIDPANGNTRYDPKFQG (SEQ ID NO: 15)
CDR3: RVGYYFDYWGQGTTLTVSS SEQ ID NO: 26 (heavy chain full protein sequence)
MKCSWVIFFL MAVVTGVTSE VQLQQSGAEL VKPGASVKLS CTASGFNIKD TYMHWVKQRP

EQGLEWIGRI DPANGNTRYD PKFQGKATIT SDTSSNTAYL QLSSLTSEDT AVYYCARRVG

YYFDYWGQGT TLTVSSAKTT PPSVYPLVPG SL

SEQ ID NO: 33 (heavy chain full nucleic acid sequence)
ATGAAATGCAGCTGGGTTATCTTCTTCCTGATGGCAGTGGTTACAGGGGTCACTTCAGAGGTTCAGCTGC

AGCAGTCTGGGGCAGAACTTGTGAAACCAGGGGCCTCAGTCAAGTTGTCCTGCACAGCTTCTGGCTTCAA

CATTAAAGACACCTATATGCACTGGGTGAAGCAGAGGCCTGAACAGGGCCTGGAGTGGATTGGAAGGATT

GATCCTGCGAATGGTAATACTAGATATGACCCAAAATTCCAGGGCAAGGCCACTATAACATCAGACACAT

-continued

```
CCTCCAACACAGCCTACCTGCAGCTCAGCAGCCTGACATCTGAGGACACTGCCGTCTATTACTGTGCTAG

GCGGGTGGGGTACTACTTTGACTACTGGGGCCAAGGCACCACTCTCACAGTCTCCTCAGCCAAAACGACA

CCCCCATCTGTCTATCCCCTGGTCCCTGGAAGCTTGGG

Trans mAb-#25
Light chain CDRs
                                                                (SEQ ID NO: 16)
CDR1: KSSQSVLYSSDLKNYLA (SEQ ID NO: 17)
CDR2: WASTRES (SEQ ID NO: 18)
CDR3: HQYLSSYT SEQ ID NO: 27 (light chain full protein sequence)
MESQTQVFLS LLLWVSGTCG NIMMTQSPSS LAVSAGEKVT MSCKSSQSVL YSSDLKNYLA

WYQQKPGQSP TLLIYWASTR ESGVPDRFTG SGSGTDFTLT ISSVQAEDLA VYYCHQYLSS

YTFGGGTKLE IKRADAAPTV SIFPPSSK

SEQ ID NO: 34 (light chain full nucleic acid sequence)
ATGGAATCACAGACTCAGGTCTTCCTCTCCCTGCTGCTCTGGGTATCTGGTACCTGTGGGAACATTATGA

TGACACAGTCGCCATCATCTCTGGCTGTGTCTGCAGGAGAAAAGGTCACTATGAGCTGTAAGTCCAGTCA

AAGTGTTTTATACAGTTCAGATCTGAAGAACTACTTGGCCTGGTACCAGCAGAAACCAGGGCAGTCTCCT

ACACTGCTGATCTATTGGGCATCCACTAGGGAATCTGGTGTCCCTGATCGCTTCACAGGCAGTGGATCTG

GGACAGATTTTACTCTTACCATCAGCAGTGTACAAGCTGAAGACCTGGCAGTTTATTACTGTCATCAATA

CCTCTCCTCGTACACGTTCGGAGGGGGGACCAAGCTGGAAATAAAACGGGCTGATGCTGCACCAACTGTA

TCCATCTTCCCACCATCCAGTAAGC

Trans mAb-#69
Light chain CDRs
                                                                (SEQ ID NO: 19)
CDR1: KSSQSLLYTGNQKNYLA (SEQ ID NO: 20)
CDR2: WASTRES (SEQ ID NO: 21)
CDR3: QQYYSYPWT SEQ ID NO: 28 (light chain full protein sequence)
MDSQAQVLML LLLWVSGTCG DIVMSQSPSS LAVSVGEKVT MSCKSSQSLL YTGNQKNYLA

WYQQKPGQSP KLLIYWASTR ESGVPDRFTG SGSGTDFTLT ISSVKAEDLA VYYCQQYYSY

PWTFGGGTKL EIKRADAAPT VSIFPPSSKL G

SEQ ID NO: 35: (light chain full nucleic acid sequence)
ATGGATTCACAGGCCCAGGTTCTTATGTTACTGCTGCTATGGGTATCTGGTACCTGTGGGGACATTGTGA

TGTCACAATCTCCATCCTCCCTAGCTGTGTCAGTTGGAGAGAAGGTTACTATGAGCTGCAAGTCCAGTCA

GAGCCTTTTATATACTGGCAATCAAAAGAACTACTTGGCCTGGTACCAGCAGAAACCAGGGCAGTCTCCT

AAACTGCTGATTTACTGGGCATCCACTAGGGAATCTGGGGTCCCTGATCGCTTCACAGGCAGTGGATCTG

GGACAGATTTCACTCTCACCATCAGCAGTGTGAAGGCTGAAGACCTGGCAGTTTATTACTGTCAGCAATA

TTATAGCTATCCGTGGACGTTCGGTGGAGGCACCAAGCTGGAAATCAAACGGGCTGATGCTGCACCAACT

GTATCCATCTTCCCACCATCCAGTAAGCTTGGG
```

Example 2

Robust Cis, but not Trans, pT231-tau Appeared Early in Axons in MCI/AD and CTE Brains, and Further Accumulated as the Diseases Progress To examine when and where cis pT231-tau appears in AD and CTE brains, we performed double immunostaining of brain sections with cis and trans mAbs, followed by isotype secondary antibodies. trans mAb stained only at the soma of a few neurons even in normal brains, cis mAb did not stain normal brains, but robustly detected signals in straight neurites of MCI neurons, which further accumulated and localized in distorted neurites of AD neurons (FIGS. 4A-4C). Notably, this pattern is similar to that detected by polyclonal cis and trans antibodies described in Nakamura et al. (*Cell* 149: 232-244, 2012), confirming not only the specificity of the cis and trans mAbs, but also indicating that cis, but not trans mAbs target the early pathogenic conformation in human MCI and AD. Staining brain sections of 8 sport- and 8 veteran-related CTE provided by Dr. McKee (Liliang et al., *J Surg Res* 160: 302-307, 2010; Chen et al., *Cancer Res* 73: 3951-3962, 2013) showed that robust cis, but not trans, p-tau was readily detected at neurites in stage II and further accumulated at stage III (FIGS. 4D-4I). These cis-positive neurites were confirmed to be axons by co-staining with the axon marker neurofilament or the dendrites marker MAP2. Notably, very rare neurons had both cis and trans p-tau, supporting that they are readily interconverted in vivo. Thus, cis appears very early in AD and CTE.

Example 3

Figure 4:
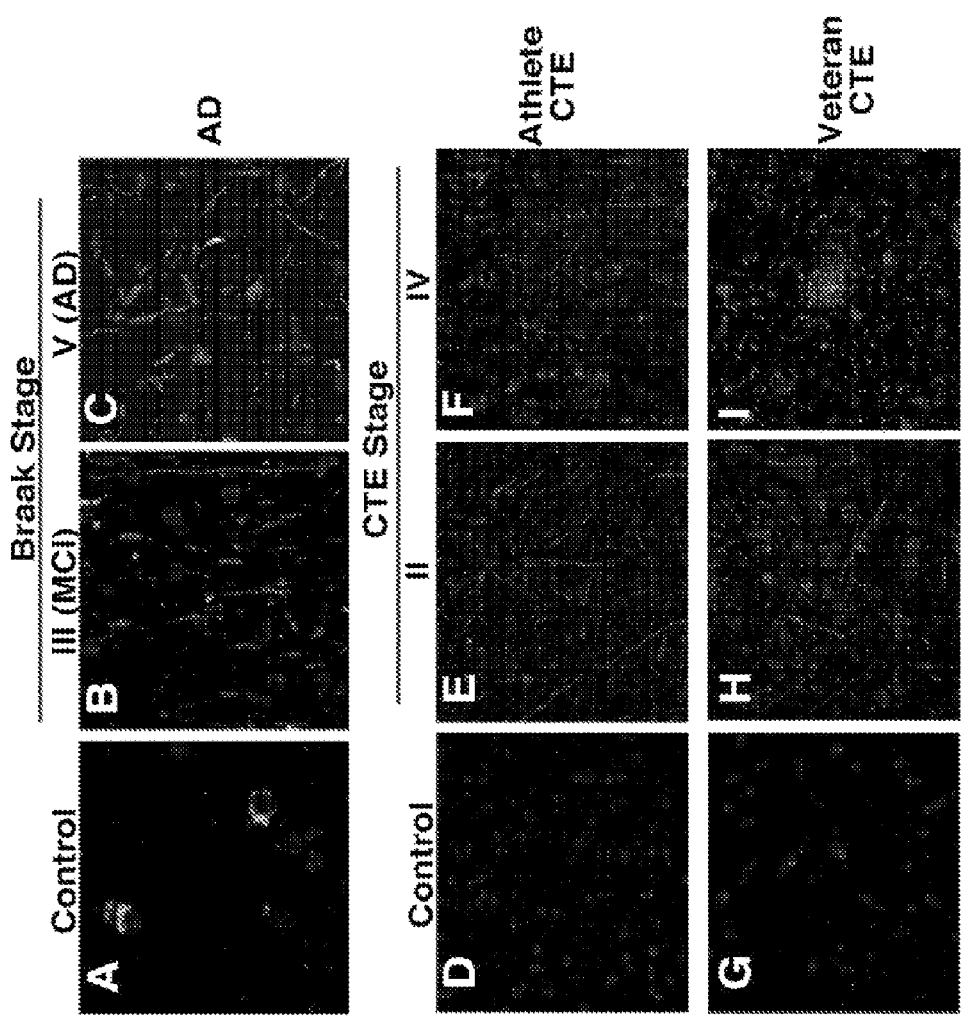
FIGS. 4A-4I are immunostaining results showing prominent cis but not trans p-tau especially in neuritis during progression of human AD and CTE. The same human brain sections were double immunostained with cis and trans mAbs with different IgG subtypes. While trans p-tau localized at the soma of a very limited number of neurons (B and C) even in normal controls, cis p-tau appeared early and accumulated and localized to neuritis (panels B, C, E, F, H, and I) during progression of AD and CTE.
Figures 5A, 5B, 5C, 5D, 5E:
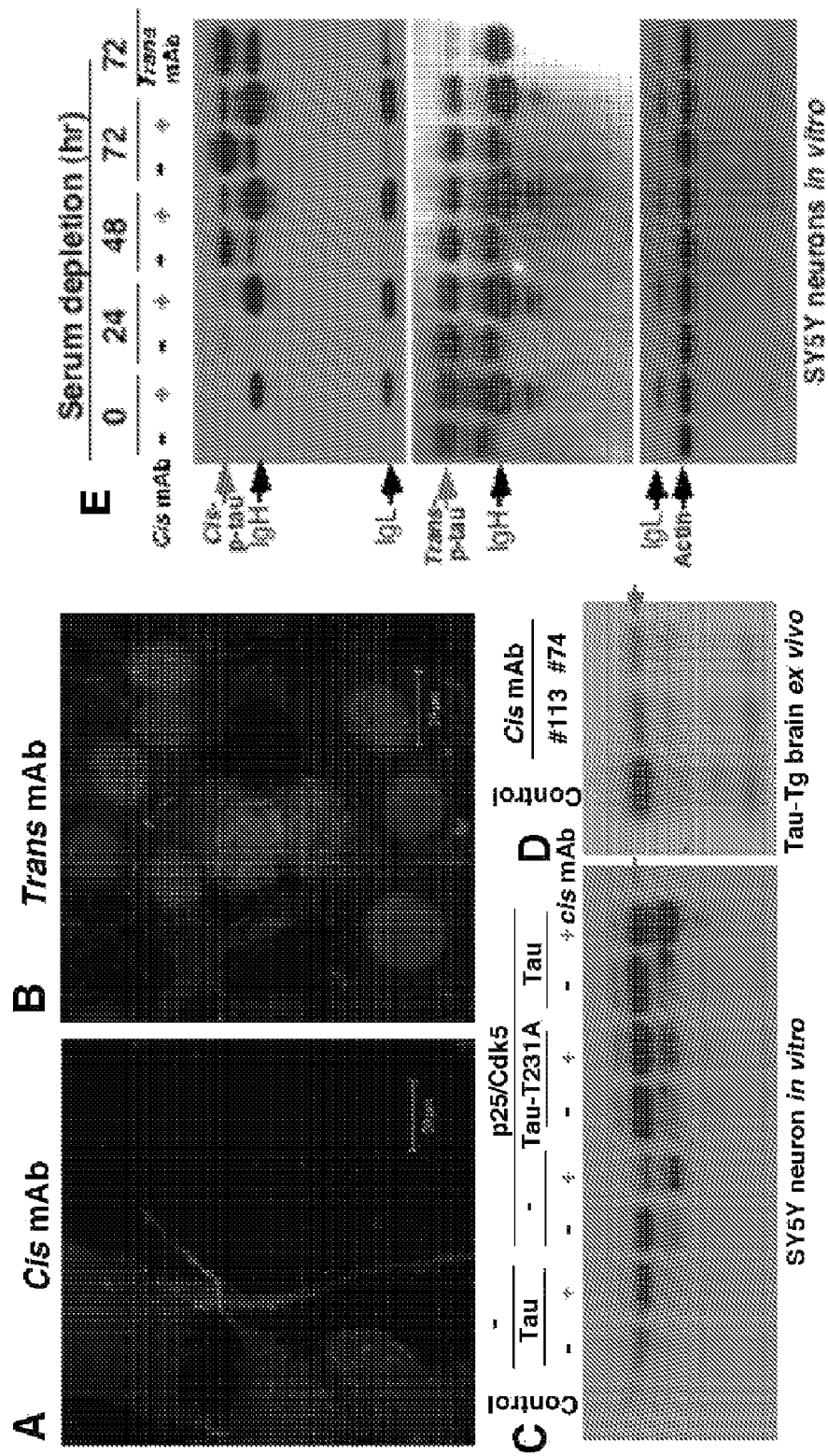
FIGS. 5A-5E are results showing that cis and trans mAbs localized to expected neuronal compartments and cis mAb reduced tau levels in a pT231-dependent manner in vitro and ex vivo.

Cis and Trans mAbs Entered Neurons and Reached Different Neuronal Compartments and Cis mAb Reduced Tau Levels in a pT232 Dependent Manner in vitro and ex vivo To determine whether cis and trans mAbs could enter neurons and reach the expected neuronal compartments, human SY5Y neurons were transfected with tau and p25/Cdk5 (tau kinase) or vector controls, followed by addition of mAbs to culture media for 48 hours before being subjected to immunostaining only with secondary antibodies or immunoblotting. Both cis and trans mAbs were readily detected not only in neurons, but also in different neuronal compartments. Cis mAb was mainly detected in neurites, whereas trans mAb was mainly detected in the soma (FIGS. 5A and 5B), as expected in MCI and AD brains (FIG. 4). More interestingly, cis mAbs significantly reduced total levels of endogenous and exogenous tau only after p25/Cdk5 overexpression, without obvious effects on tau T231A mutant (FIG. 5C). Addition of cis mAbs to culture media of human wild-type Tau-Tg mouse hippocampal slices also dramatically reduced tau levels (FIG. 5D). In addition, when SY5Y neurons were subjected to serum depletion, a stress condition similar to traumatic brain injury (TBI), it was found that cis pT231-tau in SY5Y neurons was markedly increased in a time-dependent manner by serum depletion, but such increase was effectively abrogated by cis, but not trans mAb (FIG. 5E). Thus, cis mAb reduced tau levels in vitro and ex vivo.

Example 4

Figures 6A, 6B, 6C, 6D, 6E:
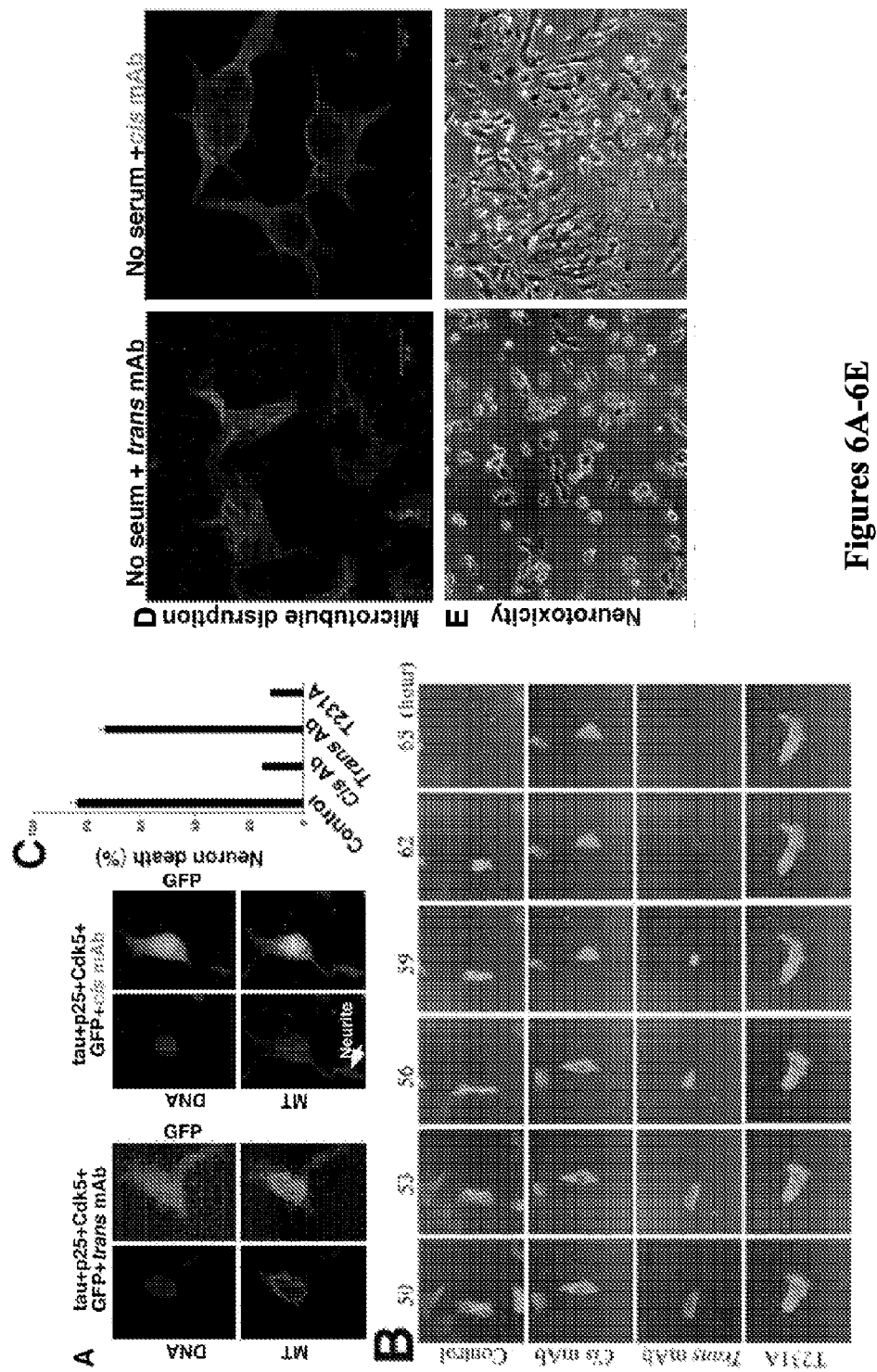
FIGS. 6A-6E are results showing that cis but not trans mAb potently suppressed microtubule disruption and neurotoxicity induced by p-tau and serum depletion.

Cis but not Trans mAb Potently Suppressed Microtubule Disruption and Neurotoxicity Induced by p-tau in Neurons To examine whether cis mAb could affect the ability of p-tau to induce microtubule disruption and neurotoxicity, we co-transfected SY5Y cells with p25/Cdk5, tau and GFP and added cis or trans mAb for 48-72 hours, followed by immunostaining for tubulins and DNA (FIG. 6A). In addition, we co-transfected SY5Y neurons with Cdk5-p25 and GFP-tau or its T231A mutant, then added cis or trans mAb, followed by live-cell confocal imaging for cell morphology and neurotoxicity (FIGS. 6B and 6C). Both assays clearly showed that cis, but not trans mAbs potently suppressed microtubule disruption (FIG. 6A) and neurotoxicity (FIGS. 6B and 6C) induced by p-tau in neurons; most GFP-tau-positive cells were dead in control and trans mAb-treated cells, with the microtubule (MT) network collapsing around the nucleus (FIG. 6A). Most cis mAb-treated GFP-tau-positive cells survived well, even with the MT network in the neurite (FIG. 6B, arrow in FIG. 6C). When added to culture media, cis but not trans mAb also effectively suppressed microtubule disruption and neurotoxicity in SY5TY neurons induced by serum depletion (FIGS. 6D and 6E).

Example 5

Figures 7A, 7B:
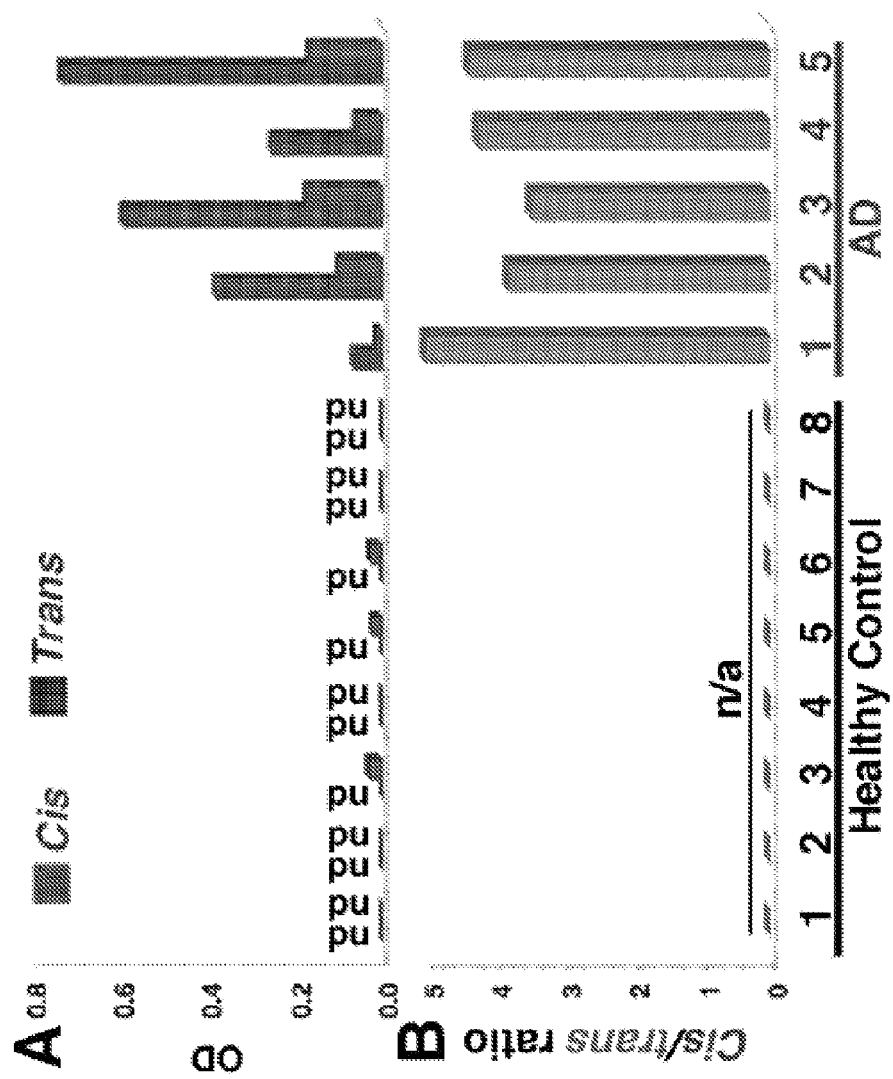
FIGS. 7A-7B show the prominent presence of CSF cis pT231-tau with cis/trans ratios consistently elevated in AD patients.

Cis pT231-tau is Prominently Present in the Extracellular Cerebrospinal Fluid (CSF) in AD Patients CSF pT231-tau is an early AD biomarker. To assay CSF pT231-tau conformations, the cis and trans pT231-tau was measured in CSFs using INNOTEST hTau ELISA kit (Innogenetics) with cis or trans Ab as the detecting antibody. In all 8 control CSFs, there was no detectable cis pT231-tau, but small amounts of the trans pT231-tau detected in 3 out of 8 cases (FIG. 7A), which might be expected because the trans is not associated with neurofibrillary tangles (NFTs). Strikingly, in advanced AD patients, trans and especially cis pT231-tau were markedly increased (FIG. 7A), consistent with what is seen in brain tissues (FIG. 4). Furthermore, although there was a wide inter-individual variation in cis or trans levels, the cis:trans ratios were very similar among AD patients (FIG. 7B).

Example 6

Figure 11:
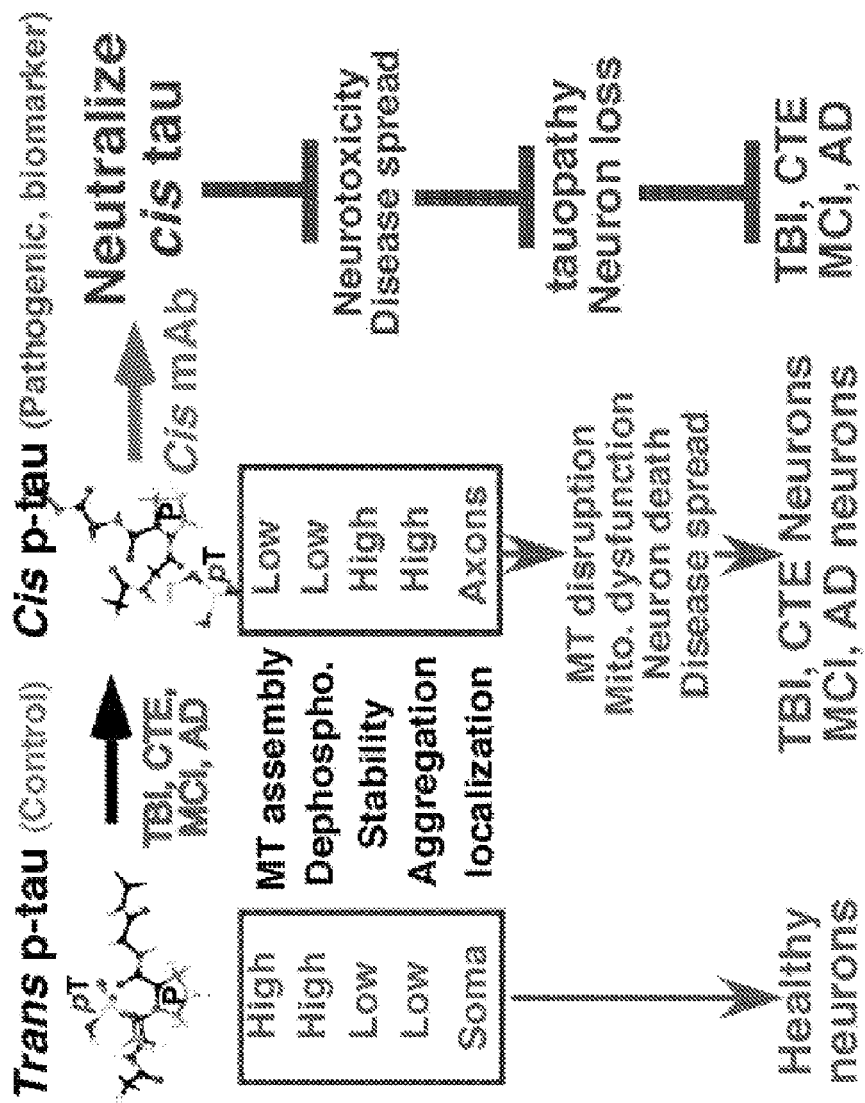
FIG. 11 is a chart showing how cis pT231-tau mAb can be used for early diagnosis and treatment of tauopathies in TBI/CTe and MCI/AD.
Figure 12:
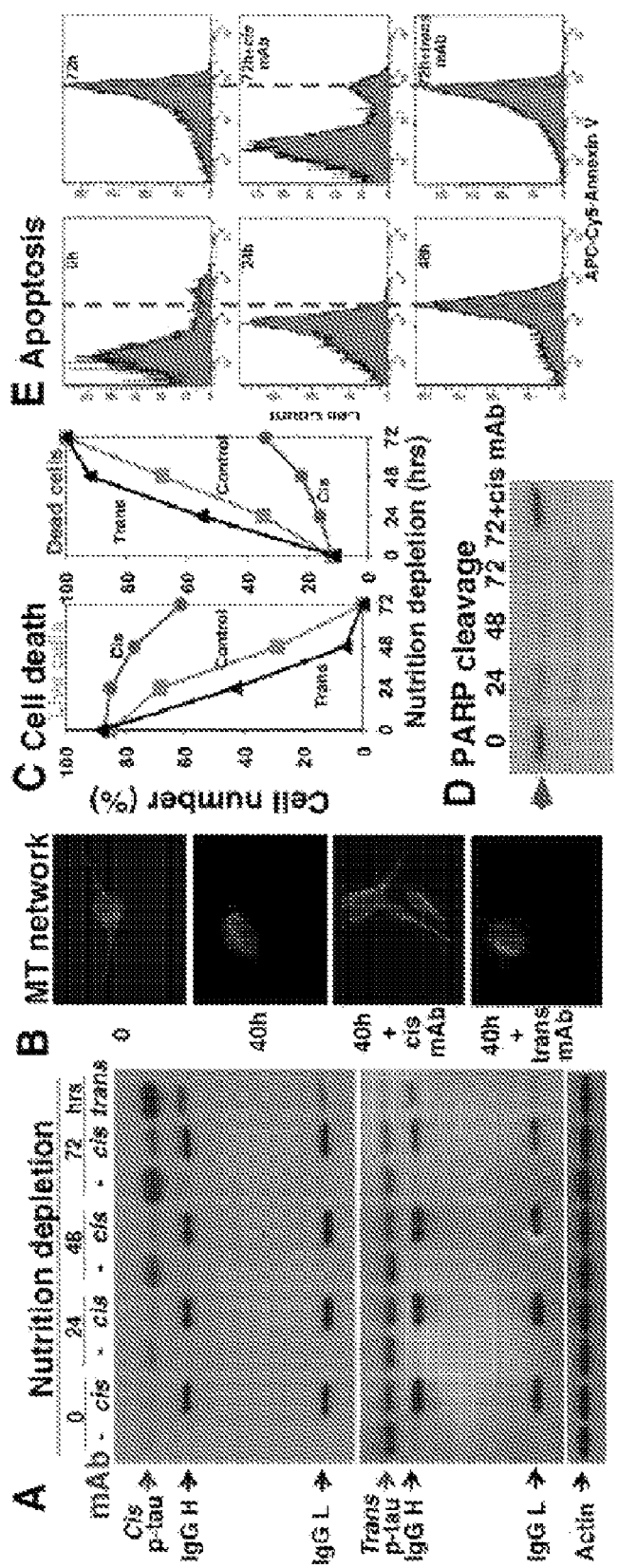
FIGS. 12A-12E are results showing that cis, but not trans mAb effectively neutralized the ability of p-tau to induce microtubule disruption, neuron death, and apoptosis after neuron stress such as nutrition depletion. Nutrition depletion induced cis, but not trans, pT231-tau, but both isomers were effectively removed by their respective mAb treatment (FIG. 12A). cis mAb effectively inhibited stress-induced microtubule disruption (FIG. 12B), neuron death by live and dead cell dye staining (FIG. 12C), and apoptosis by PARP cleavage (FIG. 12D) or annexin V FCAS (FIG. 12E), whereas trans mAb enhanced the phenotypes.

Evaluation of the Potential of Cis Tau mAb to Stop Brain Injury and its Spread in TBI Mouse Model and the Potential of Serum Cis pT231-tau Levels to Identify Patients with Significant TBI We have developed innovative peptide chemistries to create the first cis and trans pT231-tau antibodies to visualize Pin1-catalyzed conformational changes (FIG. 11). Notably, cis, but not trans, pT231-tau appears early in MCI neurons and further accumulates in axons of only degenerating neurons as AD progresses, correlating well with cognitive deficits. Moreover, cis, but not trans, pT231-tau loses its normal microtubule-assembling ability, and gains toxic function, being resistant to dephosphorylation and degradation and prone to aggregation (FIG. 11). Thus cis pT231-tau is an early and pathogenic event in MCI and AD. We have now developed neutralizing cis and trans pT231-tau monoclonal antibodies (mAbs) that were highly effective to eliminate their respective p-tau isomers in neurons and even in mouse TBI brains.

Given our promising efficacy results using cis tau mAb to treat single severe TBI mice, we will systematically evaluate the potential of cis tau mAb and its dosing requirements to stop brain injury and its spread in mouse models of repeated mild TBI at different severities by following cis pT231-tau in the brain, CSF and serum, and its relationships with behavioral and pathological changes at various times following cis mAb treatment.

Given that serum tau levels appear to correlate with TBI severity[38-41] and that our preliminary results suggest that cis p-tau, with trans as a control, may be a better biomarker than total tau, we will further improve our ELISA to assay cis and trans p-tau and total tau in 30-50 patients acutely after severe TBI and matched controls. This might eventually provide a sensitive method for identifying TBI patients for cis tau mAb therapy.

The expected outcomes would constitute an innovative conformation-specific biomarker and immunotherapy against the very early, secreted and toxic cis pT231-tau in tauopathy, raising the unique opportunity of halting or preventing tauopathy and memory loss in TBI, CTE and AD patients at early stages.

Example 7

Cis mAb not Only Effectively Eliminated Cis pT231-tau Induction, but Also Neutralized its Ability to Induce Axonal Microtubule Disruption, Mitochondrial Transport Defects and Eventually Apoptosis Under Various Neuron Stresses We found that various neuronal stresses such as hypoxia or nutrition depletion robustly induced, in a time-dependent manner, cis pT231-tau, then MT network disruption and eventually cell death by apoptosis, as shown by live (green)/dead (red) cell assay kit (Abcam) and annexin 5 FACS (FIG. 12A-12E). Our live-cell video imaging also confirmed time-dependent MT collapse and defects in axonal transport of mitochondria (data not shown). Strikingly, cis mAb treatment almost fully eliminated cis p-tau induction, and also efficiently rescued axonal MT disruption, mitochondrial transport defects, and apoptosis, while trans mAb removed trans p-tau and accelerated the phenotypes, without cross-depletion (FIG. 12). The ability of cis p-tau to induce apoptosis is consistent with previous evidence that caspases and apoptosis are present in human AD neurons (Gervais et al., Cell 97: 395-406, 1999). Similarly, the ability of cis mAb to eliminate cis p-tau and reduce total tau is consistent with our finding that cis p-tau is more stable than trans (Nakamura et al., Cell 149: 232-244, 2012), and that the antibody complex can be recognized by TRIM21 for protein degradation (Mallery et al., PNAS 107: 19985-1998590, 2010; McEwan et al., Bioessays 33: 803-809, 2011).

Example 8

Figure 13:
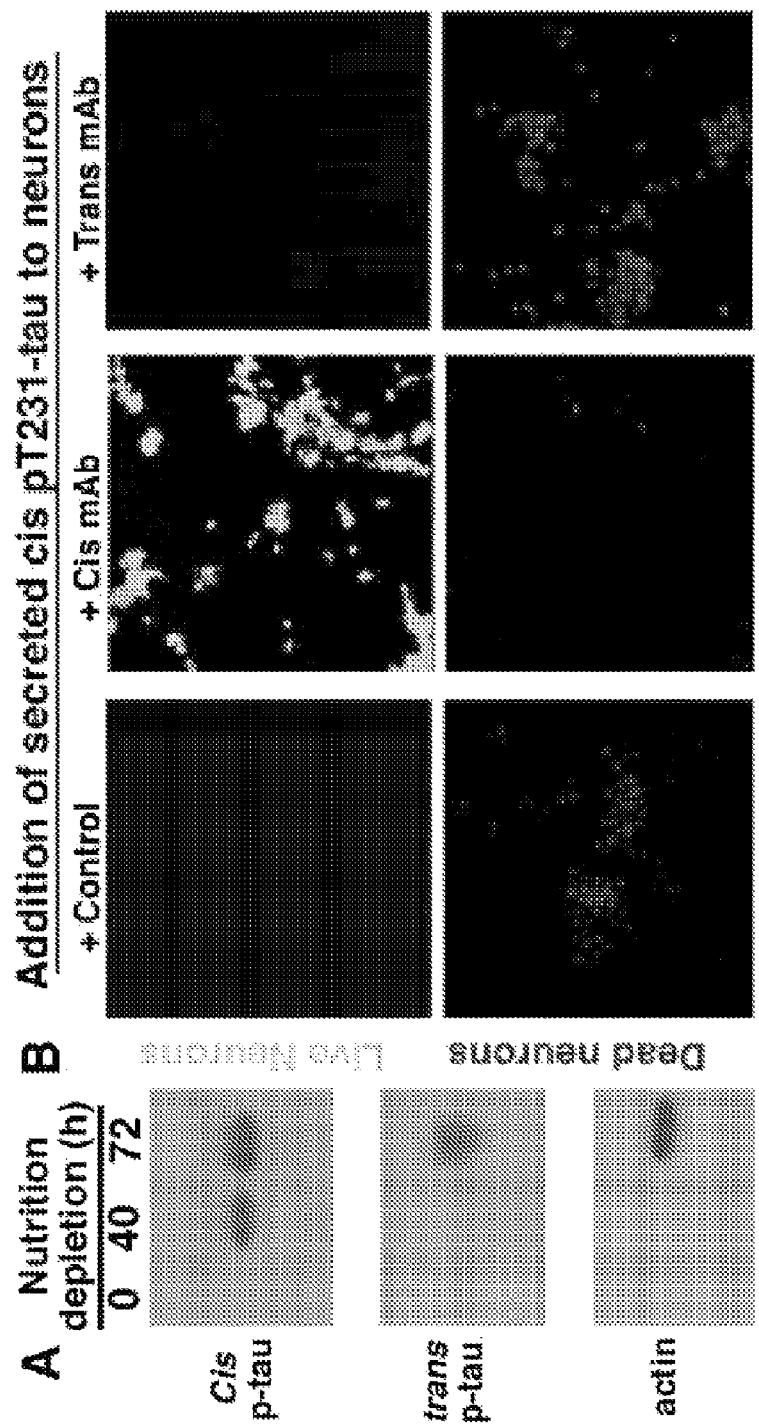
FIGS. 13A and 13B are results showing that cis, but not trans, mAb fully blocked secreted cis p-tau from inducing neurotoxicity in recipient neurons. cis, but not trans, p-tau was secreted into culture media at 48 hours after nutrient depletion (FIG. 13A). Cell culture media collected at 48 hours were incubated with cis or trans mAb or control, followed by removing the mAb using protein G before adding to recipient neurons for 3 days (FIG. 13B).

Cis, but not Trans, mAb Effectively Prevented Cis pT231-tau Secreted from Stressed Neurons from Inducing Neurotoxicity in Recipient Neurons Since abundant pT231-tau are present in CSF of AD patients and cultured neurons secrete tau into media via an unconventional mechanism, we examined whether neurons secreted cis and trans p-tau upon stresses. Indeed, stressed neurons secreted cis, but not trans pT231-tau into media at 40 hr before cell death at 72 hr, when both cis and trans p-tau as well as actin were released (FIG. 13A). More importantly, when added to healthy neurons for 3 days, the cis-containing media killed neurons by apoptosis. Pretreatment of the media with cis, but not trans, mAb, followed by depleting mAb with protein G, fully rescued neuronal death (FIG. 13B).

Example 9

Figure 14:
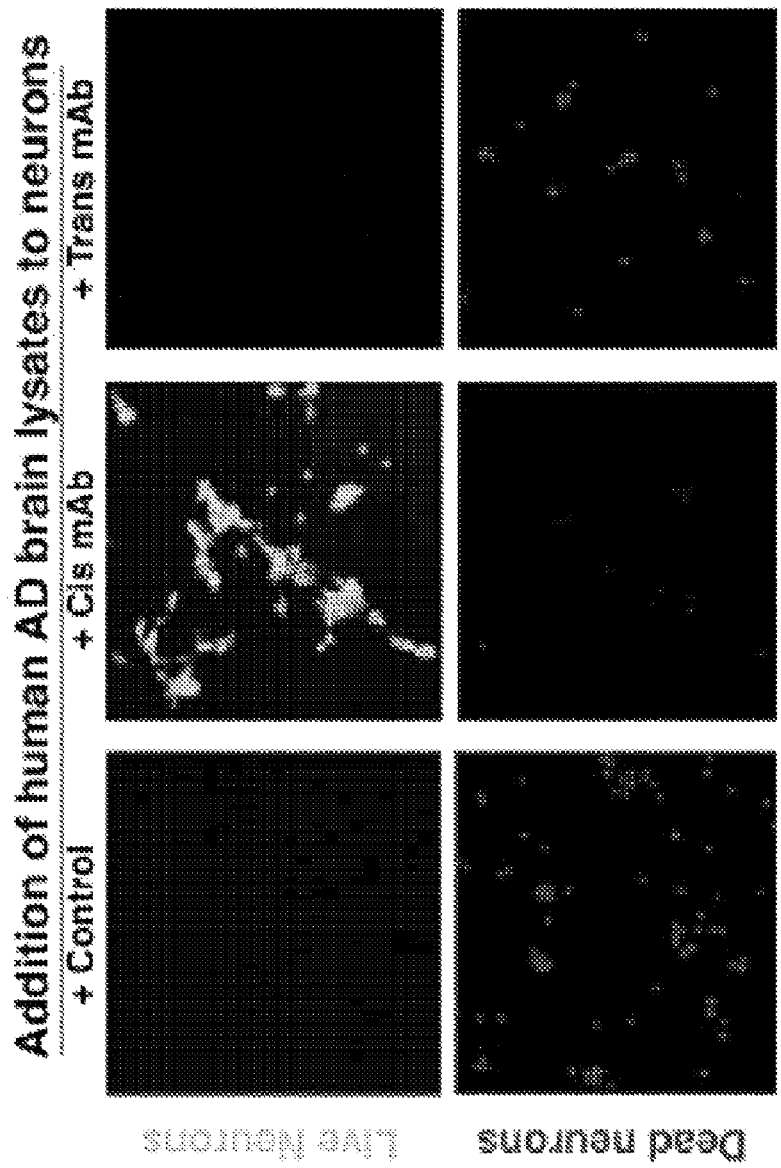
FIG. 14 is a series of immunostaining results showing that cis, but not trans, mAb fully blocked human AD brain lysates from inducing neurotoxicity in recipient neurons. Human AD brain lysates were incubated with cis or trans mAb, followed by removing the mAb using protein G before adding to recipient neurons for 3 days.

Cis, but not Trans, mAb Effectively Prevented Human AD or CTE Brain Lysates from Inducing Neurotoxicity in Recipient Neurons To examine whether human AD brains also contained toxic cis pT231-tau, we added human AD brain lysates to cultured neurons and detected cis pT231-tau in recipient neurons, but not cis-tau when control brain lysates were used. More importantly, AD, but not normal, brain lysates induces apoptosis in recipient neurons, which was fully rescued by pretreatment of AD brain lysates with cis, but not trans, mAb (FIG. 14). Similar results were also obtained with human CTE brain lysates.

Example 10

Figure 15:
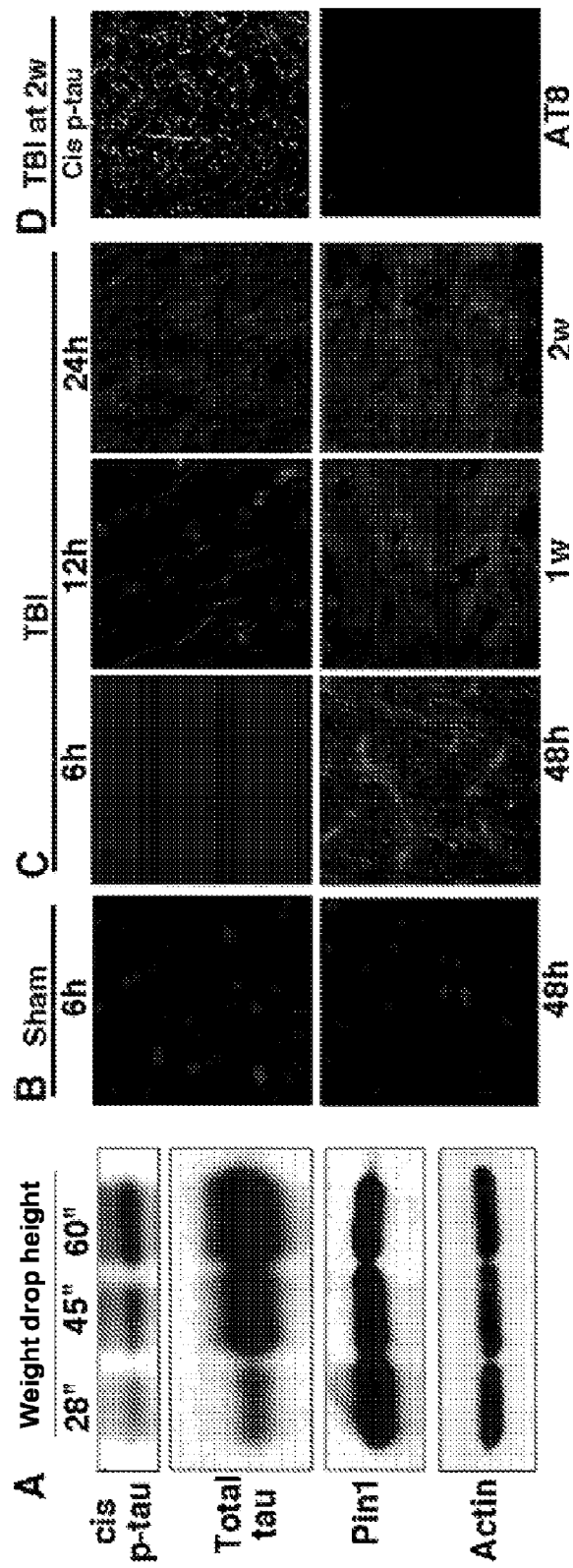
FIG. 15A-15D are results showing that cis p-tau increases with TBI severity and appears long before other tau epitopes in TBI mouse brains.
Figure 16:
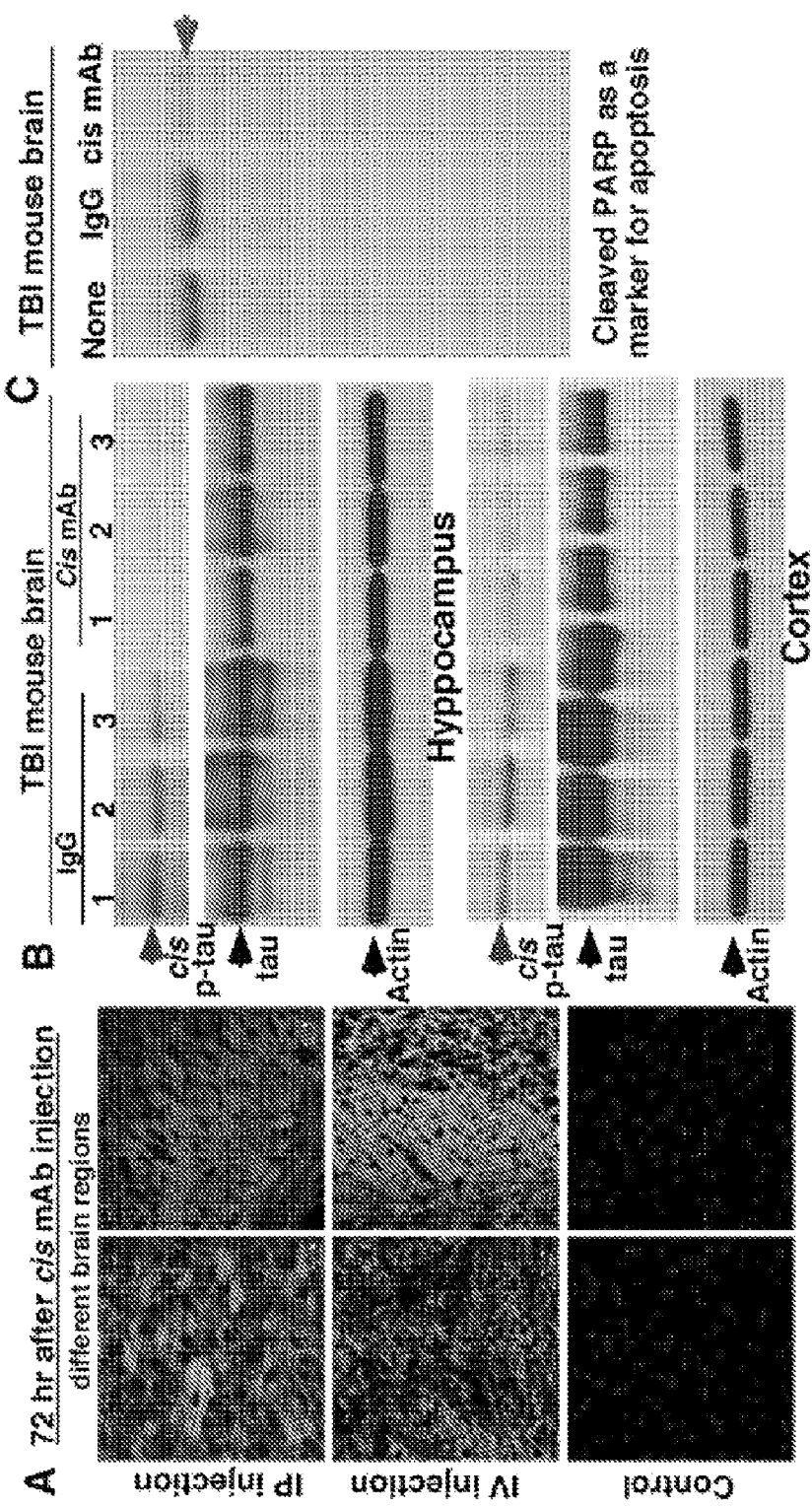
FIG. 16A-16C are results showing that cis mAb effectively eliminated cis pT231-tau induction and inhibited cell death after single severe TBI in mouse brains. 72 hours after IP or IV injection of biotin-cis mAb, mouse brain sections were stained for biotin-cis mAb (FIG. 16A). Three mice were subjected to single severe TBI, and treated with cis mAb or control IgG every four days for three times, followed by immunoblotting for cis p-tau and total tau (FIG. 16B) or cleaved PARP as a marker for apoptosis (FIG. 16C) two weeks after TBI.
Figure 17:
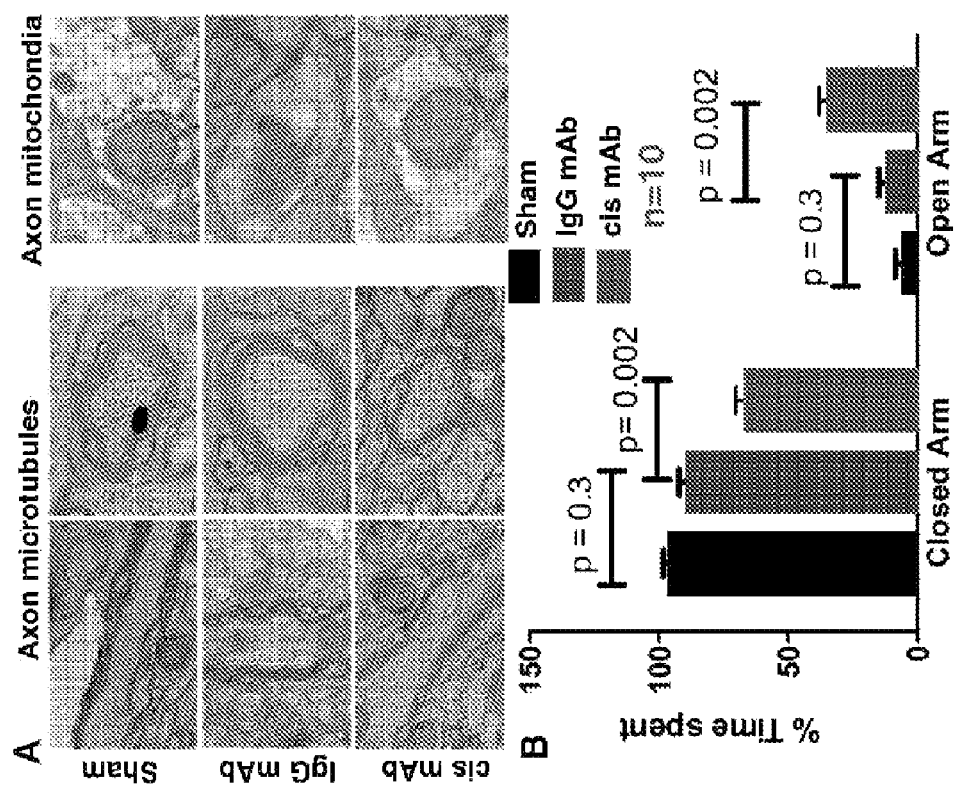
FIGS. 17A and 17B are results showing that cis mAb effectively restored microtubule disruption, mitochondrial destruction and compulsive behavioral defects after single severe TBI. Mice were subjected to single severe TBI and treated with cis mAb or control IgG every four days for three times for two weeks for electron microscopy (FIG. 17A), and then weekly for two months for behavioral tests (FIG. 17B).

Cis pT231-tau Increased with the Severity of TBI and Appeared in Axons Long Before Tangle-Related Epitopes in TBI Mouse Brains To examine the relationship between cis p-tau and TBI severity, we tested cis p-tau in brains 48 hr after TBI using a weight-drop device at different highs to induce different severity of closed head brain injury in mice, mimicking sport-related TBI. cis and total tau robustly increased with increasing TBI severity 48 hr after TBI (FIG. 15A), which is consistent with our findings that cis p-tau is resistant to degradation. Robust cis p-tau was also found 48 hr after blast-induced TBI, mimicking military-related TBI. Time course studies showed that after severe TBI, cis, but not trans, p-tau was surprisingly induced 12 hrs later and continued to increase with time, being maintained at least for 2 weeks (FIGS. 15B and 15C). cis-positive neurites were again axons, not dentrites. Notably, we could not find any tangle-related epitopes using mAb we have used, including ATB, AT180, TG3, AT100, MC1, Alz50 or PHF1 (FIG. 15D), which take a long time to appear, if ever, after TBI in WT mice.

Example 11

Figure 10:
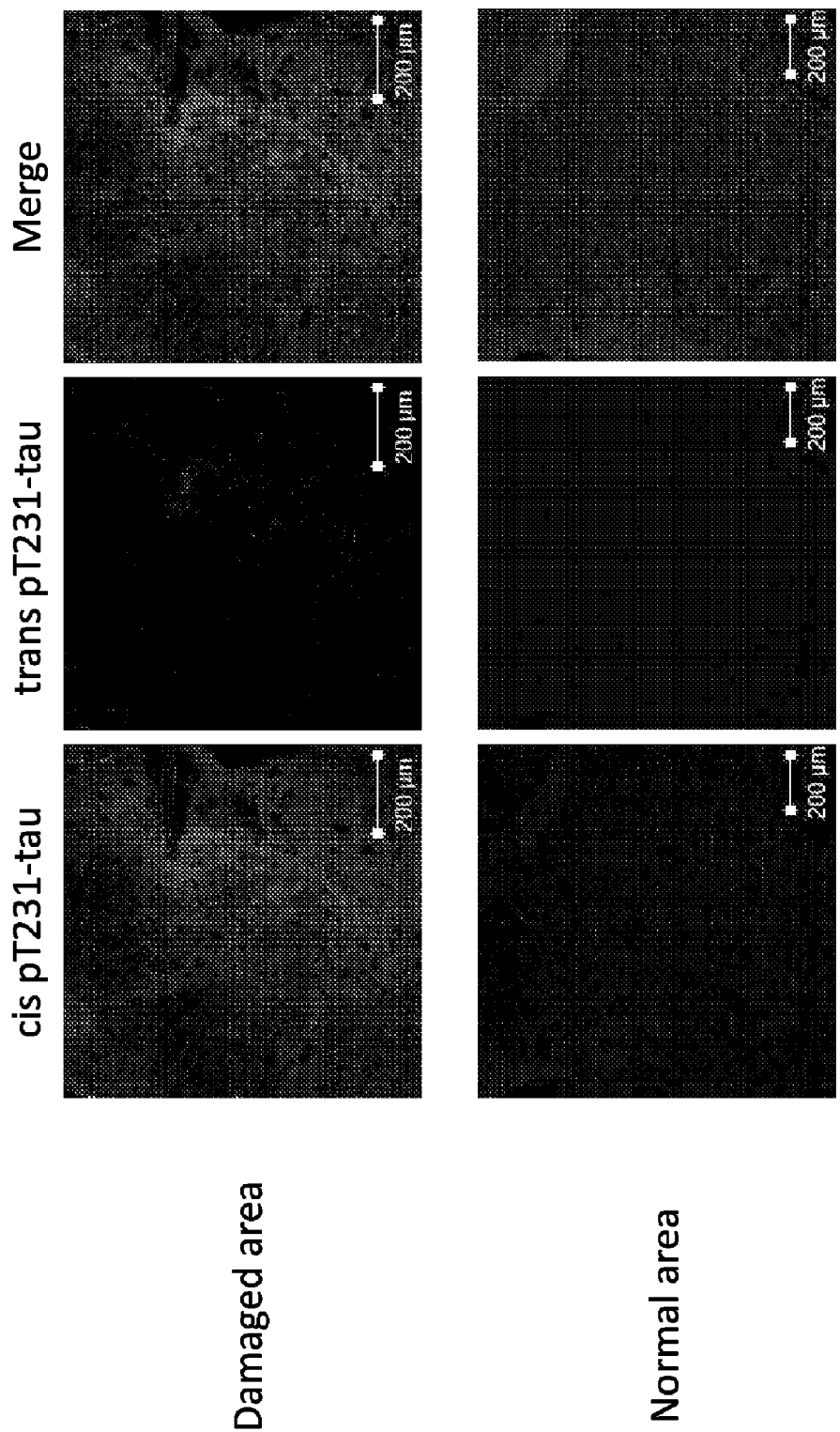
FIG. 10 is a series of immunostaining results showing prominent cis but not trans p-tau in neurons in the damaged brain area after a stroke. The same mouse brain sections were double immunostained with cis and trans mAbs with different IgG subtypes. Cis p-tau (lighter color) appeared early only in the damaged area, but not non-damaged area.

Cis mAb not Only Eliminated Cis pT231-tau, but also Restored Axonal MT Disruption, Mitochondrial Transport Defects, Apoptosis and Even Brain Function After Severe TBI in Mice To examine if cis mAb entered and eliminated cis pT231-tau and its toxicity in TBI mouse brains, we first administered i.p. or i.v. biotinated cis mAb to B6 mice and detected cis mAb 3 day later. The injected mAb was readily detected in brains (FIG. 9A). We next treated mice with I.P. 250 μg cis mAb every 4 days for 3 times after severe TBI and analyzed brains 14 days later. Strikingly, cis mAb effectively prevented TBI-induced cis pT231-tau induction and reduced total tau in mouse brains (FIG. 9B). Moreover, cis mAb, but not control IgG, treatment effectively restored axonal MT disruption and mitochondrial destruction (FIG. 10A) and even apoptosis, as assayed by PARP cleavage (FIG. 9C).

To examine whether cis mAb restored brain function after severe TBI, we used the elevated plus maze, which has widely been used to assay anxiety-related compulsive behavior in mice. 2 months after severe TBI, mice treated with IgG showed a decrease in closed arm activity and an increase in open arm activity, reflecting anxiety-related compulsive behavior, indicative of frontal cortex-related dysfunction, but cis mAb-treated mice and shame mice had not significantly different (FIG. 10B), indicating that cis mAb is able to restore TBI-induced brain function. Thus, cis mAb was highly effective in eliminating cis p-tau and its neurotoxicity, and restoring brain function in neuron and mouse models of TBI, consistent with previous work indicating that tau mAbs can enter neurons in brains (Yanamandra et al., *Neuron* 80(2): 402-414, 2013; Krishnamurthy et al., *Front Psychiatry* 2: 59, 2011; Mohamed et al., *J Neurosci Res* 69: 110-116, 2002) and that mAb can trigger target degradation in cells (Mallery et al., *PNAS* 107: 19985-1998590, 2010; McEwan et al., *Bioessays* 33: 803-809, 2011).

Other Embodiments

From the foregoing description, it will be apparent that variations and modifications may be made to the invention described herein to adopt it to various usages and conditions. Such embodiments are also within the scope of the following claims.

All publications, patent applications, and patents mentioned in this specification are herein incorporated by reference to the same extent as if each independent publication, patent application, or patent was specifically and individually indicated to be incorporated by reference.

From the foregoing description, one skilled in the art can easily ascertain the essential characteristics of this invention; can make various changes and modifications of the invention to adapt it to various usages and conditions. Thus, other embodiments are also within the claims.

The invention claimed is:

1. An isolated conformation-specific antibody or antibody fragment thereof, wherein said antibody or antibody fragment comprises:
   (a) a heavy chain variable region comprising the heavy chain CDRs of SEQ ID NOs:1-3, and a light chain variable region comprising the light chain CDRs of SEQ ID NOs:4-6; or
   (b) a heavy chain variable region comprising the heavy chain CDRs of SEQ ID NOs:7-9, and a light chain variable region comprising the light chain CDRs of SEQ ID NOs:10-12; and
   wherein said isolated antibody or antibody fragment thereof binds specifically to the cis conformation of phosphorylated-Threonine231-tau protein (pT231-tau).

2. The isolated antibody or antibody fragment thereof of claim 1, wherein the antibody or antibody fragment is a single chain antibody.

3. A pharmaceutical composition comprising the antibody or antibody fragment thereof of claim 1 and a pharmaceutically acceptable carrier.

4. A method of treating a tauopathy, traumatic brain injury (TBI), or stroke, said method comprising administering to a subject in need thereof the antibody or antibody fragment of claim 1, in an amount sufficient to treat said tauopathy, TBI, or stroke.

5. The method of claim 4, wherein said subject is predisposed to or is at an early stage of said tauopathy.

6. The method of claim 5, further comprising determining the levels of CSF t-tau, pT181-tau, Aβ42, or ApoE4 in the subject.

7. The method of claim 5, wherein said subject is predisposed by a history of repeated brain trauma.

8. A method for monitoring a therapeutic response in a subject treated with the antibody or antibody fragment of claim 1, said method comprising measuring the level of cis pT231-tau or cis:trans pT231-tau ratio in a sample obtained from said subject, wherein a decrease in the level of cis pT231-tau or cis:trans pT231-tau ratio is indicative of an effective therapeutic response to said antibody or antibody fragment.

9. The method of claim 8, further comprising measuring the levels of one or more of CSF t-tau, pT181-tau, Aβ42, or ApoE4.

10. A method of diagnosing a subject as having a tauopathy or having a predisposition to a tauopathy, said method comprising:
    a. measuring the level of cis pT231-tau or cis:trans pT231-tau ratio in a sample obtained from said subject,
    b. comparing said level of cis pT231-tau or cis:trans pT231-tau ratio in said sample with a non-diseased reference sample, wherein an elevated level of cis pT231-tau or an increase in cis:trans pT231-tau ratio as compared to said non-diseased reference sample indicates that said subject has or is predisposed to have said tauopathy; and
    c. administering to said subject the antibody or antibody fragment of claim 1 in an amount sufficient to treat said tauopathy.

11. An isolated conformation-specific antibody or antibody fragment thereof, wherein said antibody or antibody fragment comprises:
    a heavy chain variable region comprising the heavy chain CDRs of SEQ ID NOs:13-15, and a light chain variable region comprising the light chain CDRs of SEQ ID NOs:16-18,
    and wherein said isolated antibody or antibody fragment thereof binds specifically to the trans conformation of phosphorylated-Threonine231-tau protein (pT231-tau).

12. The isolated antibody or antibody fragment thereof of claim 11, wherein the antibody or antibody fragment thereof is a single chain antibody.

13. A pharmaceutical composition comprising the antibody or antibody fragment thereof of claim 11 and a pharmaceutically acceptable carrier.

14. A kit for diagnosing a subject as having a tauopathy or having a predisposition to a tauopathy comprising:
    (a) a first isolated conformation-specific antibody or antibody fragment thereof comprising:
        (i) a heavy chain variable region comprising the heavy chain CDRs of SEQ ID NOs:1-3, and a light chain variable region comprising the light chain CDRs of SEQ ID NOs:4-6; or
        (ii) a heavy chain variable region comprising the heavy chain CDRs of SEQ ID NOs:7-9, and a light chain variable region comprising the light chain CDRs of SEQ ID NOs:10-12,
        wherein said first antibody or antibody fragment thereof binds specifically to the cis conformation of pT231-tau,
    (b) a second isolated conformation-specific antibody or antibody fragment thereof comprising:
        a heavy chain variable region comprising the heavy chain CDRs of SEQ ID NOs:13-15, and a light chain variable region comprising the light chain CDRs of SEQ ID NOs:16-18,
        wherein said second antibody or antibody fragment thereof binds specifically to the trans conformation of pT231-tau, and
    (c) instructions for the use of the first antibody or antibody fragment thereof and the second antibody or antibody fragment thereof for diagnosing said subject as having a tauopathy or having a predisposition to said tauopathy.

* * * * *

UNITED STATES PATENT AND TRADEMARK OFFICE
CERTIFICATE OF CORRECTION

PATENT NO. : 9,688,747 B2
APPLICATION NO. : 14/776924
DATED : June 27, 2017
INVENTOR(S) : Kun Ping Lu et al.

It is certified that error appears in the above-identified patent and that said Letters Patent is hereby corrected as shown below:

On the Title Page

In OTHER PUBLICATIONS, in An, replace "ribonuclease a containing a" with --ribonuclease containing a--.

In the Specification

Column 4, Lines 56-57, replace "lipopolysaccarides" with --lipopolysaccharides--;
  Line 61, replace "tramatic brain injury" with --traumatic brain injury--.

Column 7, Lines 34-35, replace "panencephalistis" with --panencephalitis--.

Column 9, Line 16, replace "epitope on of a polypeptide" with --epitope of a polypeptide--.

Column 10, Line 56, replace "nuclei for microtuble disruption" with --nuclei for microtubule disruption--.

Column 11, Line 31, replace "TBI/CTe" with --TBI/CTE--;
  Line 38, replace "12A). cis mAB effectively" with --12A). Cis mAB effectively--;
  Line 45, replace "neurons. cis, but not trans" with --neurons. Cis, but not trans--.

Column 16, Line 36, replace "immunoabsorbant assays" with --immunoabsorbent assays--.

Signed and Sealed this
Twelfth Day of February, 2019

Andrei Iancu
*Director of the United States Patent and Trademark Office*

Column 25, replace the following table:

TABLE 2

Amino acid substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; | Phe; Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; | Leu | with --

TABLE 2

Amino acid substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; | Leu |

--.

Column 31, Line 65, replace "panencephalistis" with --panencephalitis--.

Column 32, Line 30, replace "taupathy" with --tauopathy--.

Column 34, Lines 4-5, replace "subjects during before, during, and after treatment" with --subjects before, during, and after treatment--.

Column 44, Line 26, replace "TBI. cis and total tau" with --TBI. Cis and total tau--;
        Line 28, replace "15C). cis-positive" with --15C). Cis-positive--;
        Line 34, replace "not dentrites" with --not dendrites--;
        Line 36, replace "ATB, AT180" with --AT8, AT180--;
        Line 48, replace "biotinated" with --biotinylated--;
        Lines 65-66, replace "and shame mice had not significantly different" with --and sham mice had no significant difference--.

SEQUENCE LISTING

```
<160> NUMBER OF SEQ ID NOS: 35

<210> SEQ ID NO 1
<211> LENGTH: 5
<212> TYPE: PRT
<213> ORGANISM: Mus musculus

<400> SEQUENCE: 1

Ser Tyr Trp Ile His
1               5

<210> SEQ ID NO 2
<211> LENGTH: 17
<212> TYPE: PRT
<213> ORGANISM: Mus musculus

<400> SEQUENCE: 2

Val Ile Asp Pro Ser Asp Ser Tyr Thr Arg Tyr Asn Gln Lys Phe Lys
1               5                   10                  15

Gly

<210> SEQ ID NO 3
<211> LENGTH: 16
<212> TYPE: PRT
<213> ORGANISM: Mus musculus

<400> SEQUENCE: 3

Trp Glu Val Asp Tyr Trp Gly Gln Gly Thr Thr Leu Thr Val Ser Ser
1               5                   10                  15

<210> SEQ ID NO 4
<211> LENGTH: 16
<212> TYPE: PRT
<213> ORGANISM: Mus musculus

<400> SEQUENCE: 4

Arg Ser Ser Gln Ser Leu Val His Ser Asp Gly Asn Thr Tyr Leu His
1               5                   10                  15

<210> SEQ ID NO 5
<211> LENGTH: 7
<212> TYPE: PRT
<213> ORGANISM: Mus musculus

<400> SEQUENCE: 5

Lys Val Ser Asn Arg Phe Ser
```

```
<210> SEQ ID NO 6
<211> LENGTH: 9
<212> TYPE: PRT
<213> ORGANISM: Mus musculus

<400> SEQUENCE: 6

Ser Gln Ser Thr His Val Pro Trp Thr
1               5

<210> SEQ ID NO 7
<211> LENGTH: 6
<212> TYPE: PRT
<213> ORGANISM: Mus musculus

<400> SEQUENCE: 7

Ser Gly Tyr Tyr Trp Asn
1               5

<210> SEQ ID NO 8
<211> LENGTH: 16
<212> TYPE: PRT
<213> ORGANISM: Mus musculus

<400> SEQUENCE: 8

Tyr Ile Ser Tyr Asp Gly Ser Asn Asn Tyr Asn Pro Ser Leu Lys Asn
1               5                   10                  15

<210> SEQ ID NO 9
<211> LENGTH: 17
<212> TYPE: PRT
<213> ORGANISM: Mus musculus

<400> SEQUENCE: 9

Leu Arg Arg Asp Ala Tyr Trp Gly Gln Gly Thr Leu Val Thr Val Ser
1               5                   10                  15

Ala

<210> SEQ ID NO 10
<211> LENGTH: 11
<212> TYPE: PRT
<213> ORGANISM: Mus musculus

<400> SEQUENCE: 10

Arg Ala Ser Gln Asp Ile Ser Asn Tyr Leu Asn
1               5                   10

<210> SEQ ID NO 11
<211> LENGTH: 7
<212> TYPE: PRT
<213> ORGANISM: Mus musculus

<400> SEQUENCE: 11

Tyr Thr Ser Arg Leu His Ser
1               5

<210> SEQ ID NO 12
<211> LENGTH: 9
<212> TYPE: PRT
<213> ORGANISM: Mus musculus

<400> SEQUENCE: 12

Gln Gln Gly Asn Thr Leu Pro Trp Thr
```

<210> SEQ ID NO 13
<211> LENGTH: 5
<212> TYPE: PRT
<213> ORGANISM: Mus musculus

<400> SEQUENCE: 13

Asp Thr Tyr Met His
1               5

<210> SEQ ID NO 14
<211> LENGTH: 17
<212> TYPE: PRT
<213> ORGANISM: Mus musculus

<400> SEQUENCE: 14

Arg Ile Asp Pro Ala Asn Gly Asn Thr Arg Tyr Asp Pro Lys Phe Gln
1               5                   10                  15

Gly

<210> SEQ ID NO 15
<211> LENGTH: 19
<212> TYPE: PRT
<213> ORGANISM: Mus musculus

<400> SEQUENCE: 15

Arg Val Gly Tyr Tyr Phe Asp Tyr Trp Gly Gln Gly Thr Thr Leu Thr
1               5                   10                  15

Val Ser Ser

<210> SEQ ID NO 16
<211> LENGTH: 17
<212> TYPE: PRT
<213> ORGANISM: Mus musculus

<400> SEQUENCE: 16

Lys Ser Ser Gln Ser Val Leu Tyr Ser Asp Leu Lys Asn Tyr Leu
1               5                   10                  15

Ala

<210> SEQ ID NO 17
<211> LENGTH: 7
<212> TYPE: PRT
<213> ORGANISM: Mus musculus

<400> SEQUENCE: 17

Trp Ala Ser Thr Arg Glu Ser
1               5

<210> SEQ ID NO 18
<211> LENGTH: 8
<212> TYPE: PRT
<213> ORGANISM: Mus musculus

<400> SEQUENCE: 18

His Gln Tyr Leu Ser Ser Tyr Thr
1               5

<210> SEQ ID NO 19
<211> LENGTH: 17
<212> TYPE: PRT
<213> ORGANISM: Mus musculus -continued

```
<400> SEQUENCE: 19

Lys Ser Ser Gln Ser Leu Leu Tyr Thr Gly Asn Gln Lys Asn Tyr Leu
1               5                   10                  15

Ala

<210> SEQ ID NO 20
<211> LENGTH: 7
<212> TYPE: PRT
<213> ORGANISM: Mus musculus

<400> SEQUENCE: 20

Trp Ala Ser Thr Arg Glu Ser
1               5

<210> SEQ ID NO 21
<211> LENGTH: 9
<212> TYPE: PRT
<213> ORGANISM: Mus musculus

<400> SEQUENCE: 21

Gln Gln Tyr Tyr Ser Tyr Pro Trp Thr
1               5

<210> SEQ ID NO 22
<211> LENGTH: 163
<212> TYPE: PRT
<213> ORGANISM: Mus musculus

<400> SEQUENCE: 22

Met Gly Val Ser Leu Gln Leu Gly Thr Gln Asp Leu Thr Met Arg
1               5                   10                  15

Trp Ser Cys Ile Ile Leu Phe Leu Val Ala Thr Ala Thr Gly Val Asn
                20                  25                  30

Ser Gln Val Gln Leu Gln Gln Pro Gly Ala Glu Leu Val Lys Pro Gly
        35                  40                  45

Ala Ser Val Lys Met Ser Cys Lys Ala Ser Gly Tyr Thr Phe Thr Ser
    50                  55                  60

Tyr Trp Ile His Trp Val Lys Gln Arg Pro Gly Gln Gly Leu Glu Trp
65                  70                  75                  80

Ile Gly Val Ile Asp Pro Ser Asp Ser Tyr Thr Arg Tyr Asn Gln Lys
                85                  90                  95

Phe Lys Gly Lys Ala Thr Leu Thr Val Asp Thr Ser Ser Ser Thr Ala
            100                 105                 110

Tyr Met Gln Leu Ser Ser Leu Thr Ser Glu Asp Ser Ala Val Tyr Tyr
        115                 120                 125

Cys Thr Thr Trp Glu Val Asp Tyr Trp Gly Gln Gly Thr Thr Leu Thr
    130                 135                 140

Val Ser Ser Ala Lys Thr Thr Pro Pro Ser Val Tyr Pro Leu Ala Pro
145                 150                 155                 160

Gly Ser Leu

<210> SEQ ID NO 23
<211> LENGTH: 166
<212> TYPE: PRT
<213> ORGANISM: Mus musculus

<400> SEQUENCE: 23

Met Gly Thr Asp Gln Ser Pro Gln Ala Val Ser Ser Gly Cys Leu Leu
```

```
                1               5                   10                  15
Lys Met Lys Leu Pro Val Arg Leu Leu Val Leu Met Phe Trp Ile Pro
                20                  25                  30

Ala Ser Asn Ser Asp Val Val Met Thr Gln Thr Pro Leu Ser Leu Pro
                35                  40                  45

Val Ser Leu Gly Asp Gln Ala Ser Ile Ser Cys Arg Ser Ser Gln Ser
                50                  55                  60

Leu Val His Ser Asp Gly Asn Thr Tyr Leu His Trp Tyr Leu Gln Lys
65                  70                  75                  80

Pro Gly Gln Ser Pro Lys Leu Leu Ile Tyr Lys Val Ser Asn Arg Phe
                85                  90                  95

Ser Gly Val Pro Asp Arg Phe Ser Gly Ser Gly Ser Gly Thr Asp Phe
                100                 105                 110

Thr Leu Lys Ile Ser Arg Leu Glu Ala Glu Asp Leu Gly Val Tyr Phe
                115                 120                 125

Cys Ser Gln Ser Thr His Val Pro Trp Thr Phe Gly Gly Gly Thr Lys
                130                 135                 140

Leu Glu Ile Lys Arg Ala Asp Ala Ala Pro Thr Val Ser Ile Phe Pro
145                 150                 155                 160

Pro Ser Ser Lys Leu Gly
                165

<210> SEQ ID NO 24
<211> LENGTH: 149
<212> TYPE: PRT
<213> ORGANISM: Mus musculus

<400> SEQUENCE: 24

Met Lys Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
                20                  25                  30

Ser Gln Ser Leu Ser Leu Thr Cys Ser Val Thr Gly Tyr Ser Ile Thr
                35                  40                  45

Ser Gly Tyr Tyr Trp Asn Trp Ile Arg Gln Phe Pro Gly Asn Lys Leu
                50                  55                  60

Glu Trp Met Gly Tyr Ile Ser Tyr Asp Gly Ser Asn Asn Tyr Asn Pro
65                  70                  75                  80

Ser Leu Lys Asn Arg Ile Ser Ile Thr Arg Asp Thr Ser Lys Asn Gln
                85                  90                  95

Phe Phe Leu Lys Leu Asn Ser Val Thr Thr Glu Asp Thr Ala Thr Tyr
                100                 105                 110

Tyr Cys Ala Gly Leu Arg Arg Asp Ala Tyr Trp Gly Gln Gly Thr Leu
                115                 120                 125

Val Thr Val Ser Ala Ala Lys Thr Thr Pro Pro Ser Val Tyr Pro Leu
                130                 135                 140

Ala Pro Gly Ser Leu
145

<210> SEQ ID NO 25
<211> LENGTH: 145
<212> TYPE: PRT
<213> ORGANISM: Mus musculus

<400> SEQUENCE: 25

Met Met Ser Ser Ala Gln Phe Leu Gly Leu Leu Leu Leu Cys Phe Gln
```

```
            1               5                   10                  15
Gly Thr Arg Cys Asp Ile Gln Met Thr Gln Thr Thr Ser Ser Leu Ser
                    20                  25                  30

Ala Ser Leu Gly Asp Arg Val Thr Ile Ser Cys Arg Ala Ser Gln Asp
                35                  40                  45

Ile Ser Asn Tyr Leu Asn Trp Tyr Gln Gln Lys Pro Asp Gly Thr Val
        50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
                100                 105                 110

Thr Leu Pro Trp Thr Phe Gly Gly Gly Thr Lys Leu Glu Ile Lys Arg
                115                 120                 125

Ala Asp Ala Ala Pro Thr Val Ser Ile Phe Pro Pro Ser Ser Lys Leu
            130                 135                 140

Gly
145

<210> SEQ ID NO 26
<211> LENGTH: 152
<212> TYPE: PRT
<213> ORGANISM: Mus musculus

<400> SEQUENCE: 26

Met Lys Cys Ser Trp Val Ile Phe Phe Leu Met Ala Val Val Thr Gly
1               5                   10                  15

Val Thr Ser Glu Val Gln Leu Gln Gln Ser Gly Ala Glu Leu Val Lys
                20                  25                  30

Pro Gly Ala Ser Val Lys Leu Ser Cys Thr Ala Ser Gly Phe Asn Ile
                35                  40                  45

Lys Asp Thr Tyr Met His Trp Val Lys Gln Arg Pro Glu Gln Gly Leu
        50                  55                  60

Glu Trp Ile Gly Arg Ile Asp Pro Ala Asn Gly Asn Thr Arg Tyr Asp
65                  70                  75                  80

Pro Lys Phe Gln Gly Lys Ala Thr Ile Thr Ser Asp Thr Ser Ser Asn
                85                  90                  95

Thr Ala Tyr Leu Gln Leu Ser Ser Leu Thr Ser Glu Asp Thr Ala Val
                100                 105                 110

Tyr Tyr Cys Ala Arg Arg Val Gly Tyr Tyr Phe Asp Tyr Trp Gly Gln
                115                 120                 125

Gly Thr Thr Leu Thr Val Ser Ser Ala Lys Thr Thr Pro Pro Ser Val
            130                 135                 140

Tyr Pro Leu Val Pro Gly Ser Leu
145                 150

<210> SEQ ID NO 27
<211> LENGTH: 148
<212> TYPE: PRT
<213> ORGANISM: Mus musculus

<400> SEQUENCE: 27

Met Glu Ser Gln Thr Gln Val Phe Leu Ser Leu Leu Leu Trp Val Ser
1               5                   10                  15

Gly Thr Cys Gly Asn Ile Met Met Thr Gln Ser Pro Ser Ser Leu Ala
```

```
                    20                  25                  30
Val Ser Ala Gly Glu Lys Val Thr Met Ser Cys Lys Ser Gln Ser
        35                  40                  45

Val Leu Tyr Ser Ser Asp Leu Lys Asn Tyr Leu Ala Trp Tyr Gln Gln
    50                  55                  60

Lys Pro Gly Gln Ser Pro Thr Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys His Gln Tyr Leu Ser Ser Tyr Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Lys
145

<210> SEQ ID NO 28
<211> LENGTH: 151
<212> TYPE: PRT
<213> ORGANISM: Mus musculus

<400> SEQUENCE: 28

Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
                20                  25                  30

Val Ser Val Gly Glu Lys Val Thr Met Ser Cys Lys Ser Ser Gln Ser
        35                  40                  45

Leu Leu Tyr Thr Gly Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Pro Trp Thr Phe Gly Gly Gly Thr
        115                 120                 125

Lys Leu Glu Ile Lys Arg Ala Asp Ala Ala Pro Thr Val Ser Ile Phe
    130                 135                 140

Pro Pro Ser Ser Lys Leu Gly
145                 150

<210> SEQ ID NO 29
<211> LENGTH: 491
<212> TYPE: DNA
<213> ORGANISM: Mus musculus

<400> SEQUENCE: 29
atgggggtct ctctacagtt actaggcaca caggatctca ccatgagatg gagctgtatc    60
atcctcttct tggtagcaac agctacaggt gtcaactccc aggtccaact gcagcagcct   120
ggggctgagc tggtgaagcc tggggcttca gtgaagatgt cctgcaaggc ttctggctac   180
accttcacca gctactggat acactgggtg aagcagaggc ctggacaagg ccttgagtgg   240
```

```
atcggagtga ttgatccttc tgatagttat actaggtaca atcaaaagtt caagggcaag    300
gccacgttga ctgtagacac atcctccagc acagcctaca tgcaactcag cagcctgaca    360
tctgaggact ctgcggtcta ttactgtaca catgggagg ttgactactg gggccaaggc     420
accactctca cagtcctc agccaaaaca acaccccat cagtctatcc cctggcccct       480
ggaagcttgg g                                                         491
```

<210> SEQ ID NO 30
<211> LENGTH: 498
<212> TYPE: DNA
<213> ORGANISM: Mus musculus

<400> SEQUENCE: 30

```
atggggactg atcagtctcc tcaggctgtc tcctcaggtt gcctcctcaa aatgaagttg     60
cctgttaggc tgttggtgct gatgttctgg attcctgctt ccaacagtga tgttgtgatg    120
acccaaactc cactctccct gcctgtcagt cttggagatc aagcctccat ctcttgcaga    180
tctagtcaga gccttgtcca cagtgatgga acacctatt acattggta cctgcagaag     240 ccaggccagt ctccaaagct cctgatctac aaagtttcca accgattttc tggggtccca    300
gacaggttca gtggcagtgg atcagggaca gatttcacac tcaagatcag cagactggag    360
gctgaggatc tgggagttta tttctgctct caaagtacaa tgttccgtg acgttcggt     420 ggaggcacca agctggaaat caacgggct gatgctgcac caactgtatc catcttccca    480
ccatccagta agcttggg                                                  498
```

<210> SEQ ID NO 31
<211> LENGTH: 449
<212> TYPE: DNA
<213> ORGANISM: Mus musculus

<400> SEQUENCE: 31

```
atgaaagtgt tgagtctgtt gtacctgttg acagccattc tggtatcct gtctgatgta     60 cagcttcagg agtcaggacc tggcctcgtg aaaccttctc agtctctgtc tctcacctgc    120
tctgtcactg gctactccat caccagtggt tattactgga actggatccg gcagtttcca    180
ggaaacaaac tggaatggat gggctacata agctacgacg gtagcaataa ctacaaccca    240
tctctcaaaa atcgaatctc catcactcgt gacacatcta gaaccagtt tttcctgaag    300 ttgaattctg tgactactga ggacacagct acatattact gtgcggggtt acgacgtgat    360
gcttactggg gccaagggac tctggtcact gtctctgcag ccaaaacaac accccatca    420 gtctatccac tggcccctgg aagcttggg                                      449
```

<210> SEQ ID NO 32
<211> LENGTH: 436
<212> TYPE: DNA
<213> ORGANISM: Mus musculus

<400> SEQUENCE: 32

```
atgatgtcct ctgctcagtt ccttggtctc ctgttgctct gttttcaagg taccagatgt     60
gatatccaga tgacacagac tacatcctcc ctgtctgcct ctctgggaga cagagtcacc    120
atcagttgca gggcaagtca ggacattagc aattatttaa actggtatca gcagaaacca    180
gatggaactg ttaaactcct gatctactac acatcaagat tacactcagg agtcccatca    240
aggttcagtg gcagtgggtc tggaacagat tattctctca ccattagcaa cctggagcaa    300
```

```
gaagatattg ccacttactt tgccaacag ggtaatacgc ttccgtggac gttcggtgga    360
ggcaccaagc tggaaatcaa acgggctgat gctgcaccaa ctgtatccat cttcccacca    420
tccagtaagc ttgggg                                                    436
```

<210> SEQ ID NO 33
<211> LENGTH: 458
<212> TYPE: DNA
<213> ORGANISM: Mus musculus

<400> SEQUENCE: 33

```
atgaaatgca gctgggttat cttcttcctg atggcagtgg ttacaggggt cacttcagag     60
gttcagctgc agcagtctgg ggcagaactt gtgaaaccag ggcctcagt caagttgtcc    120 tgcacagctt ctggcttcaa cattaaagac acctatatgc actgggtgaa gcagaggcct    180
gaacagggcc tggagtggat tggaaggatt gatcctgcga atggtaatac tagatatgac    240
ccaaaattcc agggcaaggc cactataaca tcagacacat cctccaacac agcctacctg    300
cagctcagca gcctgacatc tgaggacact gccgtctatt actgtgctag cgggtgggg    360 tactactttg actactgggg ccaaggcacc actctcacag tctcctcagc caaaacgaca    420 ccccccatctg tctatcccct ggtccctgga agcttggg                           458
```

<210> SEQ ID NO 34
<211> LENGTH: 445
<212> TYPE: DNA
<213> ORGANISM: Mus musculus

<400> SEQUENCE: 34

```
atggaatcac agactcaggt cttcctctcc ctgctgctct gggtatctgg tacctgtggg     60
aacattatga tgacacagtc gccatcatct ctggctgtgt ctgcaggaga aaaggtcact    120
atgagctgta agtccagtca aagtgttta tacagttcag atctgaagaa ctacttggcc    180
tggtaccagc agaaaccagg gcagtctcct acactgctga tctattgggc atccactagg    240
gaatctggtg tccctgatcg cttcacaggc agtggatctg ggacagattt tactcttacc    300
atcagcagtg tacaagctga agacctggca gtttattact gtcatcaata cctctcctcg    360
tacacgttcg gaggggggac caagctggaa ataaaacggg ctgatgctgc accaactgta    420
tccatcttcc caccatccag taagc                                          445
```

<210> SEQ ID NO 35
<211> LENGTH: 453
<212> TYPE: DNA
<213> ORGANISM: Mus musculus

<400> SEQUENCE: 35

```
atggattcac aggcccaggt tcttatgtta ctgctgctat gggtatctgg tacctgtggg     60
gacattgtga tgtcacaatc tccatcctcc ctagctgtgt cagttggaga aaaggttact    120
atgagctgca gtccagtca gagccttta tatactggca atcaaaagaa ctacttggcc    180
tggtaccagc agaaaccagg gcagtctcct aaactgctga tttactgggc atccactagg    240
gaatctgggg tccctgatcg cttcacaggc agtggatctg ggacagattt cactctcacc    300
atcagcagtg tgaaggctga agacctggca gtttattact gtcagcaata ttatagctat    360
ccgtggacgt tcggtggagg caccaagctg gaaatcaaac gggctgatgc tgcaccaact    420
gtatccatct tcccaccatc cagtaagctt ggg                                 453
```